(12) United States Patent
Barker et al.

(10) Patent No.: US 10,596,193 B2
(45) Date of Patent: Mar. 24, 2020

(54) COPPER (I) COMPLEXES WITH GLYCINE, PYRUVATE, AND SUCCINATE

(71) Applicant: C LAB PHARMA INTERNATIONAL, S.A., Tortola (VG)

(72) Inventors: Charles Louis Albartus Barker, Flagstaff, AZ (US); William A. Boulanger, Mahomet, IL (US)

(73) Assignee: C Lab Pharma International, S.A., Tortola (VG)

( * ) Notice: Subject to any disclaimer, the term of this patent is extended or adjusted under 35 U.S.C. 154(b) by 175 days.

(21) Appl. No.: 15/706,467

(22) Filed: Sep. 15, 2017

(65) Prior Publication Data

US 2018/0071336 A1    Mar. 15, 2018

Related U.S. Application Data

(63) Continuation-in-part of application No. 14/773,289, filed as application No. PCT/US2014/021772 on Mar. 7, 2014, now abandoned.

(60) Provisional application No. 61/774,543, filed on Mar. 7, 2013.

(51) Int. Cl.
*A61K 33/34* (2006.01)
*A61K 31/555* (2006.01)
*C07F 1/08* (2006.01)

(52) U.S. Cl.
CPC ............ *A61K 33/34* (2013.01); *A61K 31/555* (2013.01); *C07F 1/08* (2013.01); *Y02A 50/40* (2018.01); *Y02A 50/401* (2018.01); *Y02A 50/402* (2018.01)

(58) Field of Classification Search
None
See application file for complete search history.

(56) References Cited

U.S. PATENT DOCUMENTS 4,270,953 A * 6/1981 Nakagawa ........... C09D 5/1643
106/150.1

FOREIGN PATENT DOCUMENTS

CN         106278916 A  *  1/2017

OTHER PUBLICATIONS

John R. J. Sorenson, Copper Chelates as Possible Active Forms of the Antiarthritic Agents, 1975, Journal of Medicinal Chemistry, vol. 19, No. 1, pp. 135-149 (Year: 1975).*

* cited by examiner

*Primary Examiner* — Nannette Holloman
(74) *Attorney, Agent, or Firm* — Rodney J. Fuller; Booth Udall Fuller, PLC

(57) ABSTRACT

The present invention is directed to a pharmaceutical and/or dietary supplement composition comprising an effective amount of a copper (I) complex with glycine, pyruvate, or succinic acid and methods of treating mitochondrial, neuromuscular, and other diseases. Also provided are pharmaceutical treatment regimes and kits comprising a copper (I) complex with glycine, pyruvate, or succinate.

9 Claims, 20 Drawing Sheets

COPPER (I) COMPLEXES WITH GLYCINE, PYRUVATE, AND SUCCINATE

RELATED APPLICATION DATA

This application is a continuation in-part of U.S. patent application Ser. No. 14/773,289, filed on Sep. 4, 2015, which is the U.S. national-stage application of International Application No. PCT/US2014/021772, filed on Mar. 7, 2014, which claims the benefit of U.S. Provisional Application No. 61/774,543, filed on Mar. 7, 2013, the contents of each of which are hereby incorporated by reference in its entirety.

TECHNICAL FIELD

This application relates to pharmaceutical and/or dietary supplement compositions comprising copper (I) complexes and the methods of preparing such copper (I) complexes. The application also encompasses methods of treating mitochondria, neuromuscular, and other diseases, and pharmaceutical and/or dietary supplement compositions and methods of treating other physical ailments and disorders, including but not limited to pain, fatigue, sleeplessness, loss of fine motor control, speech loss, inflexibility, Lyme disease, Lyme disease co-infection, gastroparesis (GP), myopathy, chronic inflammation and/or incontinence.

BACKGROUND OF THE INVENTION

Copper (as copper amino acid chelate) plays a role in transporting oxygen throughout the body. The production of collagen, which determines the integrity of bones, skin, cartilage, and tendons, is copper dependent. Copper is also crucial for making melanin, which provides color to skin and hair. Copper helps keep blood vessels elastic, is needed for the formation of elastin, functions as an iron oxidizer, and is needed for the proper functioning of vitamin C.

Copper is also an important cofactor for metalloenzymes, and is a necessary cofactor for superoxide dismutase (Beem J BIOL CHEM 249:7298 (1974)). Copper has been shown to decrease in individuals over 70 years of age and to be basically zero in cataractous lenses (Swanson BIOCHEM BIPHY RES COMM 45:1488-96 (1971)). If copper is significantly decreased, superoxide dismutase has been shown to have decreased function, thereby hampering an important protective lens mechanism (Williams PEDIAT RES 1:823 (1977)). For these and many other reasons, copper is required for optimal human health.

The two principal oxidation states of copper are +1 and +2 although some +3 complexes are known. Copper (I) compounds are expected to be diamagnetic in nature and are usually colorless, except where color results from charge transfer or from the anion. The +1 ion has tetrahedral or square planar geometry. In solid compounds, copper (I) is often the more stable state at moderate temperatures.

The copper (II) ion is usually the more stable state in aqueous solutions. Compounds of this ion, often called cupric compounds, are usually colored. They are affected by Jahn Teller distortions and exhibit a wide range of stereochemistries with four, five, and six coordination compounds predominating. The +2 ion often shows distorted tetrahedral geometry.

Complexes of copper (I) are thought to have a unique mechanism of action in promoting aerobic respiration via the electron transport chain. By causing the mitochondria in the cells to produce adenosine triphosphate (ATP) more efficiently and avoiding the production of lactic acid and ethanol that accompanies anaerobic respiration, pharmaceutical preparations and dietary supplements with copper (I) may alleviate and treat many illness and diseases. Among these diseases are those involving neuromuscular degeneration and muscle weakness. Accordingly, there is a need to develop novel copper (I) compounds that may stimulate ATP production in the mitochondria.

SUMMARY OF THE INVENTION

The objective of the present invention is to provide pharmaceutical and/or dietary supplement compositions and methods of making and using the same to treat and reduce many of the symptoms of several diseases. The compositions contain an active pharmacological ingredient comprised of a copper (I) complex. The pharmacologically active ingredient may be administered alone or in combination with additional active or inert agents or therapies (e.g. other anti-inflammatory agents, diluents, and/or excipients).

The pharmacologically active ingredient of the present invention possesses a chemical structure selected from:

Formula (I):

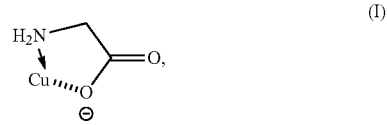

Formula (II):

Formula (III):

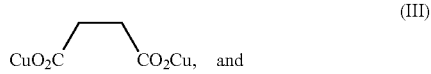

Formula (IV):

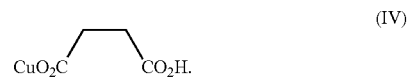

The present invention is also directed to a method of treating diseases and other physical ailments or disorders. In a preferred embodiment the method comprises the step of administering to a subject in need thereof a copper (I) complex having a formula of Formula (I), Formula (II), Formula (III) or Formula (IV) to reduce and/or treat a disease or physical ailment or disorder. Preferably the disease or physical ailment being treated is a mitochondrial or neuromuscular disease. The treated diseases or disorders (or other physical ailments) include, but are not limited to fibromyalgia, spinal cord injury, multiple sclerosis, muscular dystrophy, stroke, rheumatoid arthritis, pain, fatigue, sleeplessness, loss of fine motor control, speech loss, inflexibility, Lyme disease, Lyme disease co-infection, gastroparesis (GP), chronic inflammation, myopathy, chronic inflammation, and/or incontinence. It is also preferable that the subject be diagnosed with one of the diseases and/or disorders prior to treatment.

The present invention encompasses a method of treating a mitochondrial disease selected from the group consisting of Myoclonic Epilepsy with Ragged Red Fibers (MERRF);

Mitochondrial Myopathy, Encephalopathy, Lactacidosis, and Stroke (MELAS); Diabetes mellitus and deafness (DAD); Maternally Inherited Diabetes and Deafness (MIDD), Leber's Hereditary Optic Neuropathy (LHON); chronic progressive external ophthalmoplegia (CPEO); Leigh Disease; Kearns-Sayre Syndrome (KSS); Friedreich's Ataxia (FRDA); Co-Enzyme Q10 (Co-Q10) Deficiency; Neuropathy, ataxia, retinitis pigmentosa, and ptosis (NARP); Myoneurogenic gastrointestinal encephalopathy (MNGIE); Complex I Deficiency; Complex II Deficiency; Complex III Deficiency; Complex IV Deficiency; Complex V Deficiency; and other myopathies that effect mitochondrial function.

Preferred embodiments of the compositions of the present invention, including recommended dosages and methods of use, are more fully described below in the Detailed Description.

BRIEF DESCRIPTION OF THE DRAWINGS

Illustrative and exemplary embodiments of the invention are shown in the drawings in which.

Figure 1:
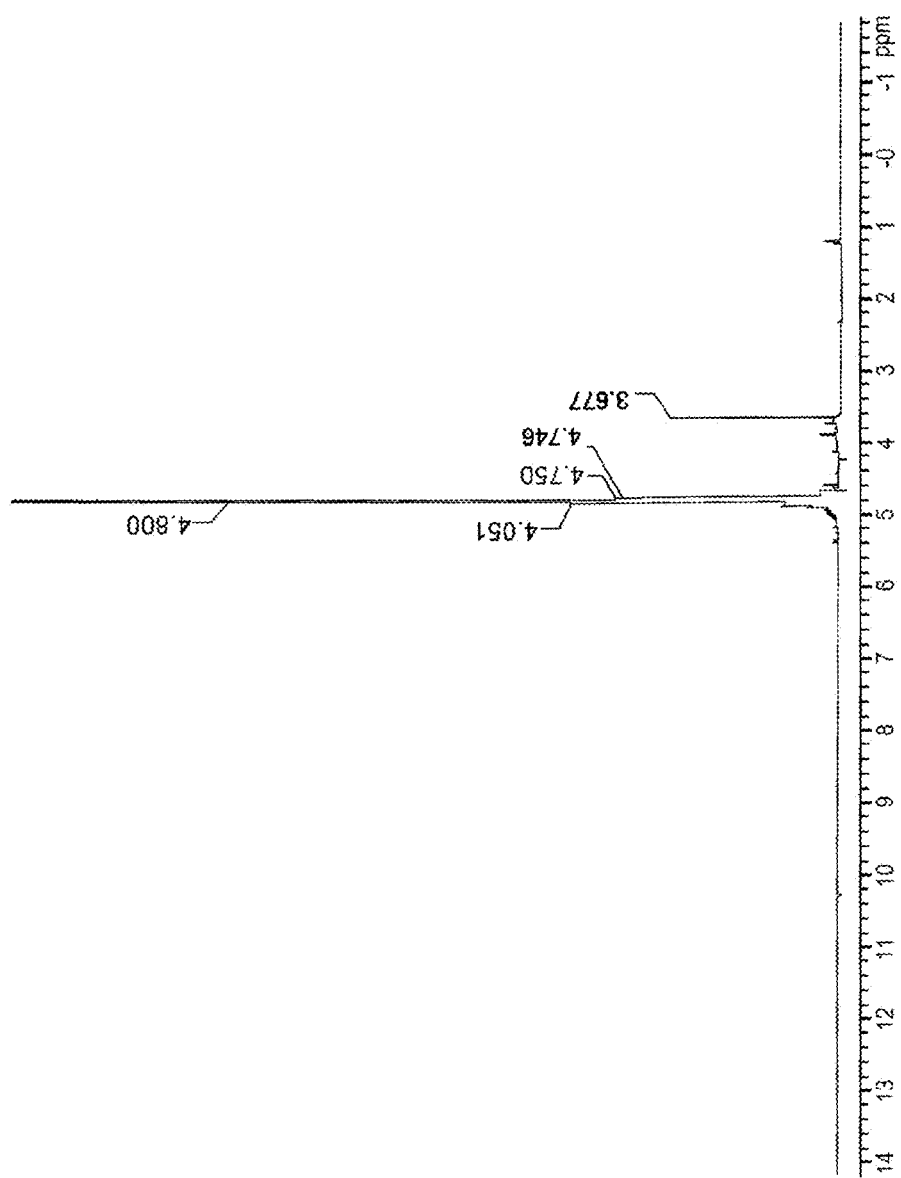
FIG. 1 depicts a proton NMR of an embodiment of a copper (I) glycinate complex dissolved in deuterium oxide ($D_2O$).

Elements and facts in the figures are illustrated for simplicity and have not necessarily been rendered according to any particular sequence or embodiment.

DETAILED DESCRIPTION OF THE PREFERRED EMBODIMENTS

The verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one."

The terms "copper (I) complex" and "copper (I) compound" as used herein are interchangeable and refer to a chemical compound in which copper is present in its +1 oxidation state and interacts with at least one other element through ionic or covalent bonding.

The term "extended release" herein refers to any formulation or dosage form that comprises an active drug and which is formulated to provide a longer duration of pharmacological response after administration of the dosage form than is ordinarily experienced after administration of a corresponding immediate release formulation comprising the same drug in the same amount. Controlled release formulations include, inter alia, those formulations described elsewhere as "controlled release", "delayed release", "sustained release", "prolonged release", "programmed release", "time release" and/or "rate controlled" formulations or dosage forms. Further for the purposes of this invention refers to release of an active pharmaceutical agent over a prolonged period of time, such as for example over a period of 8, 12, 16 or 24 hours.

As used herein, the term "subject" or "patient" refers to any vertebrate including, without limitation, humans and other primates (e.g., chimpanzees and other apes and monkey species), farm animals (e.g., cattle, sheep, pigs, goats and horses), domestic mammals (e.g., dogs and cats), laboratory animals (e.g., rodents such as mice, rats, and guinea pigs), and birds (e.g., domestic, wild and game birds such as chickens, turkeys and other gallinaceous birds, ducks, geese, and the like). In some embodiments, the subject is a mammal. In other embodiments, the subject is a human.

Compositions

The compositions of the present invention may comprise an effective amount of a copper (I) complex having a formula selected from:

Formula (I):

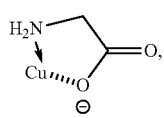
(I)

Formula (II):

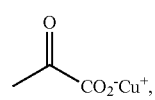
(II)

Formula (III):

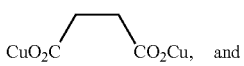
(III)

Formula (IV):

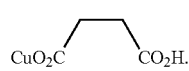
(IV)

Preferably, the pharmaceutical composition further comprises copper ascorbate (esterified Vitamin C), ascorbic acid (Vitamin C), and/or a pharmaceutically acceptable excipient (carrier). More preferably, the pharmaceutically acceptable carrier is an inert diluent.

The compositions of the present invention may comprise a delivery vehicle. Suitable delivery vehicles include a liposome, a microsome, a nanosome, a picosome, a pellet, a granular matrix, a bead, a microsphere, a nanoparticle formulation, or an aqueous solution.

Liposomes can aid in the delivery of the copper (I) compounds to a particular tissue and can also increase the blood half-life of the compounds. Liposomes suitable for use in the invention are formed from standard vesicle-forming lipids, which generally include neutral, positively or negatively charged phospholipids and, optionally, a sterol, such as cholesterol. The selection of lipids is generally guided by consideration of factors such as the desired liposome size and half-life of the liposomes in the blood stream. A variety of methods are known for preparing liposomes, for example as described in Szoka et al. (1980), *Ann. Rev. Biophys. Bioeng.* 9: 467; and U.S. Pat. Nos. 4,235,871, 4,501,728, 4,837,028, and 5,019,369, the entire disclosures of which are herein incorporated by reference.

Polyacrylates represent a further example of a suitable delivery vehicle for use in the present invention. By way of example, a terpolymer of styrene and hydroxyethyl methacrylate cross-linked with a difunctional azo-compound may be employed. The system depends on cleavage of the azo bond by intestinal microflora resulting in degradation of polymer. Similarly, a pH responsive poly (methacrylic-g-ethylene glycol) hydrogel may be employed as an oral delivery vehicle. Once inside the basic and neutral environment of the small intestine, the gels rapidly swell and dissociate.

In another embodiment, a microcapsule formulation may be employed for peroral delivery. In more detail, aqueous colloidal terpolymers of ethylacrylate/methyl methacrylate/2-hydroxyethyl methacrylate (poly (EA/MME/HEMA), for example as synthesized by emulsion polymerization technique(s) may be employed. These polymers exhibit delayed release profiles, which were characterized by a long lag time and subsequent rapid release of the entrapped moiety.

In another embodiment, orally administered nanoparticles may serve as suitable delivery vehicles. By way of example, loaded nanoparticles may be entrapped into pH sensitive microspheres, which serve to deliver the incorporated nanoparticle to the desired site of action. Nanoparticles have a large specific surface, which is indicative of high interactive potential with biological surfaces. Thus, bioadhesion can be induced by binding nanoparticles with different molecules. By way of example, nanoparticles may be prepared from gliadin protein isolate from wheat gluten and then conjugated with lectins (glycoproteins of non-immune origin which provide specific bioadhesion). Accordingly, nanoparticles are provided, which have a high capacity for non-specific interaction with intestine.

The compositions of the present invention may take the form of differently sized particles. In some embodiments, particles are microparticles (aka microspheres or microsomes). In general, a "microparticle" refers to any particle having a diameter of less than 1000 µm. In some embodiments, particles are nanoparticles (aka nanospheres or nanosomes). In general, a "nanoparticle" refers to any particle having a diameter of less than 1000 nm. In some embodiments, particles are picoparticles (aka picospheres or picosomes). In general, a "picoparticle" refers to any particle having a diameter of less than 1 nm. In some embodiments, particles are micelles.

In one embodiment, a delivery vehicle based on an albumin-chitosan mixed matrix microsphere-filled coated capsule formulation may be employed. In this regard, a preparation of a copper (I) compound of the invention is filled into hard gelatin capsules and enteric coated.

In one embodiment, albumin microspheres may be employed as the oral delivery system.

In one embodiment, squalane oil-containing multiple emulsions may be employed.

In one embodiment, poly(lactide-co-glycolide) microspheres may be employed as the oral delivery vehicle.

In one embodiment, a delivery coating comprising a mixture of pH-responsive enteric polymer (Eudragit S) and biodegradable polysaccharide (resistant starch) in a single layer matrix film may be employed.

In one embodiment, delivery capsules such as liposomes, micro- or nanocapsules (e.g. chitosan nanocapsules) may be chemically modified with poly(ethylene glycol) (PEG). The typical degree of PEGylation is in the range of 0.1% to 5%, such as 0.5% to 2%, for example 0.5% or 1%. The presence of PEG, whether alone or grafted to chitosan, improves the stability of the delivery capsules in the gastrointestinal fluids.

PEGylated delivery vehicles such as liposomes, micro- or nanocapsules have an intrinsic ability to accumulate at disease sites and facilitate transfection of target cells. Unlike many viral vectors, PEGylated liposomes are generally considered to be non-immunogenic.

In one embodiment, a branched PEGylating reagent is employed as branched PEG protecting groups are more effective than linear PEG molecules.

In one embodiment, the copper (I) compounds of the invention are prepared with carriers that will protect the compound against rapid elimination from the body, such as an extended release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

The materials can also be obtained commercially from Alza Corporation and Nova Pharmaceuticals, Inc.

Other embodiments of the invention are directed to a single crystalline form of the copper (I) complexes characterized by a combination of the characteristics of any of the single crystalline forms discussed herein. The characterization can be any combination of one or more of the XRPD, TGA, DSC, moisture sorption/desorption measurements and single crystal structure determination described for a particular crystalline form. For example, the single crystalline form of a copper (I) complex can be characterized by any combination of the XRPD results regarding the 2θ position of the major peaks in an XRPD scan; and/or any combination of one or more of the unit cell parameters derived from data obtained from the single crystal structure analysis. DSC determinations of the temperature associated with the maximum heat flow during a heat flow transition and/or the temperature at which a sample begins to undergo a heat flow transition may also characterize the crystalline form. Weight change in a sample and/or change in sorption/desorption of water per molecule of a copper (I) complex of the present invention as determined by moisture sorption/desorption measurements over a range of relative humidity can also characterize a single crystalline form of a copper (I) complex.

Examples of combinations of single crystalline form characterizations using multiple analytical techniques include the 2θ positions of at least one of the major peaks of an XRPD scan and the temperature associated with the maximum heat flow during one or more heat flow transitions observed by a corresponding DSC measurements; the 2θ positions of at least one of the major peaks of an XRPD scan and one or more weight losses associated with a sample over a designated temperature range in a corresponding TGA measurement; the 2θ positions of at least one of the major peaks of an XRPD scan, and the temperature associated with the maximum heat flow during one or more heat flow transitions observed by a corresponding DSC measurements, and one or more weight losses associated with a sample over a designated temperature range in a corresponding TGA measurement; the 2θ positions of at least one of the major peaks of an XRPD scan, and the temperature associated with the maximum heat flow during one or more heat flow transitions observed by a corresponding DSC measurements, one or more weight losses associated with a sample over a designated temperature range in a corresponding TGA measurement, and the change in sorption/desorption measurements over a range of relative humidity. As well, each of the aforementioned examples can replace the use of 2θ positions of at least one of the major peaks of an XRPD scan with one or more unit cell parameters of the single crystalline form.

The combinations of characterization that are discussed above can be used to describe any of the single crystalline forms of a copper (I) complex of the present invention.

The D90 particle size diameter of the copper (I) complexes of the present invention may be 1 to 500 microns; e.g., any range within 1 and 500 microns, such as 1 to 100 microns, 50 to 250 microns, 100 to 300 microns, 250 to 500 microns, etc.

Indications

The compositions of the present invention may be used to effectively treat numerous human diseases and other ailments characterized by neuromuscular degeneration and muscle weakness. These diseases are described in detail below.

The copper (I) complexes of the present invention are particularly effective in treating mitochondrial diseases. Mitochondrial diseases are often the result a deficiency in ATP production, via the oxidative phosphorylation, which makes high energy-demanding tissues or organs such as heart, brain, and muscles, the main targets for these disorders. By restoring ATP production to normal, the copper (I) complexes may prevent, treat, or reverse mitochondrial disease.

Impairments in oxidative phoshporylation are often referred to as mitochondrial dysfunction (and are associated with mitochondrial disease). They can result from hereditary and somatic mutations in nuclear genes or mtDNA, or functional impairments by drugs or toxins. Mutations in over 100 genes constituting the oxidative phosphorylation machinery are linked with mitochondrial encephalopathies in humans, which are the most common metabolic diseases with an incidence of over 1/5000 in live births.

Respiratory chain Complex I deficiency is a cause of mitochondrial diseases in many cases. Twenty-five of at least fifty known genes implicated in Complex I biogenesis are found associated with mitochondrial diseases. Pathogenic mutations in structural subunits (e.g., NDUFA 1, 2, 11; NDUFS 1-4, 6-8; NDUFV 1, 2) and assembly factors (e.g., NDUFAF1-6) have been identified. Neurodegenerative diseases such as Parkinson's disease, Alzheimer's disease, and Huntington's disease are also associated with mitochondrial dysfunction. Further, mtDNA mutations are found associated with almost all types of cancers. Type 2 diabetes is also linked with declining mitochondrial function in relevant tissues such as β-cells and muscles. Type 2 diabetes represents a major clinical challenge due to the sharp rise in obesity-induced disease. Thus, in some embodiments, methods are provided for treating a mitochondrial disease or a mitochondrial dysfunction.

Symptoms of mitochondrial diseases usually include slow growth, loss of muscle coordination, muscle weakness, visual defect, hearing defects, learning disabilities, mental retardation, heart disease, liver disease, kidney disease, gastrointestinal disorders, respiratory disorders, neurological problems, and dementia.

The copper (I) complexes of the present invention may be used to treat mitochondrial diseases such as Myoclonic Epilepsy with Ragged Red Fibers (MERRF); Mitochondrial Myopathy, Encephalopathy, Lactacidosis, and Stroke (MELAS); Diabetes mellitus and deafness (DAD); Maternally Inherited Diabetes and Deafness (MIDD), Leber's Hereditary Optic Neuropathy (LHON); chronic progressive external ophthalmoplegia (CPEO); Leigh Disease; Kearns-Sayre Syndrome (KSS); Friedreich's Ataxia (FRDA); Co-Enzyme Q10 (Co-Q10) Deficiency; Neuropathy, ataxia, retinitis pigmentosa, and ptosis (NARP); Myoneurogenic gastrointestinal encephalopathy (MNGIE); Complex I Deficiency; Complex II Deficiency; Complex III Deficiency; Complex IV Deficiency; Complex V Deficiency; and other myopathies that effect mitochondrial function.

The copper (I) complexes of the present invention may also be used to treat a neuromuscular disease. The term "neuromuscular disease" refers to disorders that adversely affect muscle function and/or the control thereof by the central nervous system (CNS). In general, neuromuscular diseases encompass a wide range of physical ailments characterized by impaired muscle function. The following (non-limiting) list of conditions is generally recognized as neuromuscular diseases or conditions: multiple sclerosis, muscular dystrophy, rheumatoid arthritis, fibromyalgia, myopathy, inflammatory bowel disease (IBD), incontinence, inflexibility, impaired fine motor skills, and amyotrophic lateral sclerosis ("ALS" or Lou Gehrig's disease).

A stroke, formerly known as a cerebrovascular accident (CVA), often results in severe neurological impairment. Post-stroke, many individuals suffer one or more neurological impairments including, but not limited to: loss of fine motor control, paralysis, speech impairment/loss (aphasia and/or dysarthria), altered smell, taste, hearing, or vision, ptosis, ocular and facial muscle weakness, diminished reflexes, loss of balance, altered heart rate, apraxia, loss of memory, and/or confusion.

Three of the most prominent diseases associated with impaired neurological function are muscular dystrophy (MD), multiple sclerosis (MS), and rheumatoid arthritis (RA).

The term Muscular Dystrophy (MD) actually refers to a group of diseases characterized by muscle weakness and/or impaired muscle function. The specific diseases include, but are not limited to Becker, Duchenne, and Emery-Dreifuss. Over 100 diseases, however, display symptoms similar to MD. All are characterized by reduced muscle function and muscle weakness.

Multiple Sclerosis (MS) is an autoimmune disease diagnosed in 350,000-500,000 people in the United States. The disease is characterized by multiple areas of inflammation and scarring of the myelin in the brain and spinal cord. Patients inflicted with the disease exhibit varying degrees of neurological impairment depending on the location and extent of the myelin scarring. Typical MS symptoms include fatigue, weakness, spasticity, balance problems, bladder and bowel problems, numbness, loss of vision, tremors, and depression. Available treatments of MS generally only alleviate symptoms or delay the progression of the disability Rheumatoid Arthritis (RA) is another troublesome disorder associated with inflammation. It is signified by chronic inflammation in the membrane lining (the synovium) of the joints and/or other internal organs. These inflammatory cells can also damage bone and cartilage. For example, a joint inflicted with RA may lose its shape and alignment, which can result in the loss of range of motion. RA is characterized by pain, stiffness, warmth, redness and swelling in the joint, and other systemic symptoms like fever, fatigue, and anemia. RA currently affects roughly 1% of the entire U.S. population (approximately 2.2 million people). The pathology of RA is not fully understood, although it has been hypothesized to result from a cascade of aberrant immunological reactions.

The compositions of the present invention are particularly effective in treating Lyme disease and Lyme disease co-infections. Lyme disease is a bacterial infection (*Borrelia burgdorferi*) spread by ticks. The number of reported cases of Lyme disease, and the number of geographical areas in which it is found, has been increasing. In addition to causing arthritis, Lyme disease can also cause heart, brain, and nerve problems. Early symptoms include skin-rash, flu-like symptoms (e.g. chills, fever, swollen lymph nodes, headaches, fatigue, muscle aches/pains, and joint pain). More advanced symptoms include nerve problems and arthritis.

Lyme disease is often associated with muscle degeneration and/or muscle weakness. In one aspect of the present invention, treatment of Lyme disease in a subject with a copper (I) complex results in improved muscle health and/or muscle tone. In some embodiments, the Lyme disease is chronic Lyme disease that persists in spite of treatment with standard antibiotic treatments.

Often, ticks can become infected with multiple disease-causing microbes, resulting in co-infection. This may be a potential problem for humans, due to *Borrelia burgdorferi*, and other harmful pathogens carried and transmitted by some ticks. Possible co-infections with viruses such as *Lyme borreliosis, anaplasmosis, babesiosis*, or encephalitis may occur. It is not known how co-infection may affect disease transmission and progression, but may help in diagnosing and treating Lyme and other such diseases.

In one embodiment, the present invention is directed to a method of treating a tickborne disease with a copper (I) complex. Tickborne diseases include Babesiosis, Ehrlichiosis and Anaplasmosis, Lyme Disease, Relapsing Fever, Rocky Mountain Spotted Fever, and Tularemia.

Tickborne diseases can be found throughout the United States. For example, Lyme disease, first discovered in Connecticut in the early 1970s, has since spread to every state except Hawaii. Rocky Mountain spotted fever, a bacterial disease transmitted by the dog tick, was first identified in 1896.

One of the newest tickborne diseases to be identified in the United States is called Southern tick-associated rash illness (STARI). This disease has a bull's-eye rash similar to that found in Lyme disease, which is caused by bacteria transmitted by the deer tick. Although researchers know that the lone star tick transmits the infectious agent that causes STARI, they do not yet know what microbe causes it.

Ticks transmit ehrlichiosis and anaplasmosis, both bacterial diseases. Babesiosis is caused by parasites carried by deer ticks. These diseases are found in several states.

Tularemia, a less common tickborne bacterial disease, can be transmitted by ticks as well as other vectors (carriers) such as the deerfly. Public health experts are concerned that the bacterium that causes tularemia (*Francisella tularensis*) could be used as a weapon of bioterrorism.

Transmission of tickborne diseases is not limited to ticks. In addition, tickborne diseases may be spread via other vectors (e.g., mosquitoes, flies, or other insects), via contaminated body fluids (e.g., blood transfusions), via sexual transmission or any other number of ways.

The copper (I) complexes may be used to treat gastroparesis. Gastroparesis is a condition characterizes by the inability of the stomach to empty its contents, when there is no blockage (obstruction). The cause of gastroparesis is not known. There is some evidence that it may be caused by a disruption of nerve signals to the stomach. The condition is a complication of diabetes and of some surgeries. Risk factors associated with gastroparesis may include diabetes, gastrectomy (surgery to remove part of the stomach), systemic sclerosis, use of medication that blocks certain nerve signals (anticholinergic medication). Symptoms may include abdominal distention, hypoglycemia (in people with diabetes), nausea, premature abdominal fullness after meals, weight loss, and vomiting. If gastroparesis is caused by a condition that is reversible (e.g. pancreatitis), when the condition is resolved, the symptoms will subside. For some diabetics, better control of their blood sugar can also improve the symptoms. If there is no reversible cause, gastroparesis rarely resolves itself and the symptoms often grow more sever with time. When accompanied by motility disorders of the muscles of the small intestine, gastroparesis is particularly difficult to treat.

The invention may be used to treat an animal with a disease or physical ailment or disorder including, but not limited to, one or more of the following: fibromyalgia, multiple sclerosis, muscular dystrophy, rheumatoid arthritis, Alzheimer's, dementia, ALS, depression, pain, fatigue, sleeplessness, inflexibility, myopathy, Lyme disease, Lyme disease co-infection, gastroparesis (GP), chronic inflammation, incontinence, impaired fine motor skills, high cholesterol, low sperm count, obesity, alopecia, burns, stretch marks, scars, ADD, ADHD, and/or erectile dysfunction, wherein it is preferable that the animal is a mammal and more preferable that the mammal is a human.

In an alternate embodiment, the present invention is further directed to pharmaceutical and/or dietary supplement compositions for treating post-stroke symptoms, including, but not limited to: loss of fine motor control, paralysis, speech impairment/loss (aphasia and/or dysarthria), altered smell, taste, hearing, or vision, ptosis, ocular and facial muscle weakness, diminished reflexes, loss of balance, altered heart rate, apraxia, loss of memory, and/or confusion.

Advantageously, the present invention is further directed to pharmaceutical and/or dietary supplement compositions for promoting one or more desired health benefits. In a preferred embodiment, the compositions of the present invention promote hair growth, skin healing, scar removal, nerve growth, muscle growth, enhanced athletic performance, reduced post-traumatic healing time, post-surgery healing, and/or enhanced libido.

In one embodiment, the subject is first diagnosed with one of the diseases listed above before treatment.

Modes of Administration

Frequency of dosage may vary depending on the purity of the compound and the particular disease or physical ailment treated. However, for treatment of most diseases and physical ailments, a dosage regimen of (4) 2.5 mg capsules (for a total of 10 mg/day) containing copper (I) complexes of the present invention is preferred. As will be understood by one skilled in the art, however, the optimal dosage level for a particular subject will vary depending on a plurality of factors including the potency and activity of the pharmacologically active ingredient, as well as the age, body weight, general health, sex, diet, time of administration, route of administration and rate of excretion, drug combination (if any) and the severity of the particular disease or physical ailment undergoing therapy. Subject to the above factors, a generally effective amount of the copper (I) complexes of the present invention is between 1 mg and 20 mg per day. More preferably, the effective amount of is between 5 mg and 10 mg per day. Advantageously, the effective amount of is between 7.5 mg to 10 mg per day. Most preferably (subject to the factors listed above), the effective amount is about 10 mg/per day.

Copper (I) complexes of the present invention may also comprise a component of an overall pharmaceutical treatment regime for reducing and/or treating a disease or physical ailment or other disorder including, but not limited to: fibromyalgia, multiple sclerosis, muscular dystrophy, rheumatoid arthritis, Alzheimer's, dementia, ALS, depression, pain, fatigue, sleeplessness, inflexibility, myopathy, incontinence, impaired fine motor skills, high cholesterol, low sperm count, obesity, alopecia, burns, stretch marks, scars, ADD, ADHD, and/or erectile dysfunction, the treatment regime comprising: administering to a subject at the least the following pharmacologically active ingredient(s) within a 24-hour period: copper (I) complexes of the present invention, and optionally a pharmaceutically acceptable carrier, wherein the pharmacologically active ingredient(s) is in an amount sufficient to reduce the symptoms of the ailment.

Optionally, the pharmaceutical treatment regime including copper (I) complexes of the present invention may include (or be combined with) additional pharmacologically active ingredients or other complementary treatments in order to provide synergistic therapeutic effects. For example, copper (I) complexes of the present invention may be administered in combination with additional pharmacologically active agents including, but not limited to, non-steroidal anti-inflammatory drugs (NSAIDs), corticosteroids, disease modifying anti-rheumatic drugs (DMARDs), biologic DMARDs, and/or cyclooxygenase-2 (COX-2) inhibitors. In a preferred embodiment, copper (I) complexes of the present invention is administered in combination with ozone therapy.

The pharmaceutical and/or dietary supplement compositions of the present invention may take a variety of forms specially adapted to the chosen route of administration. The compositions may be administered orally, topically, parenterally, by inhalation or spray, or by any other conventional means. Preferably, the compositions are prepared and administered in dosage unit formulations containing conventional non-toxic pharmaceutically acceptable carriers, adjuvants and vehicles. In one preferred embodiment, the composition is administered sublingually. It is further understood that the preferred method of administration may be a combination of methods. Oral administration in the form of a capsule, pill, elixir, syrup, lozenge, troche, or the like is particularly preferred. The pharmaceutical compositions of the present invention are preferably in a form suitable for oral use, for example, as tablets, troches, lozenges, aqueous or oily suspensions, dispersible powders or granules, emulsion, hard or softgel capsules, or syrups or elixirs.

Compositions intended for oral use may be prepared according to any method known in the art for manufacture of pharmaceutical compositions, and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients suitable for the manufacture of tablets. Such excipients may include, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by techniques to delay disintegration and absorption in the gastrointestinal tract and thereby provide a sustained action over a longer period. For example, a time delay material such as glyceryl monostearate or glyceryl distearate may be utilized.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; and dispersing or wetting agents, which may be a naturally-occurring phosphatide, for example, lecithin, or condensation products of ethylene oxide with long chain aliphatic alcohols—for example, heptadecaethyleneoxycetanol, or condensation products of ethylene oxide with partial esters derived from fatty acids and hexitol anhydrides, for example polyethylene sorbitan monooleate. The aqueous suspensions may also contain one or more preservatives, for example ethyl, or n-propyl-p-hydroxybenzoate, one or more coloring agents, one or more flavoring agents, and one or more sweetening agents, such as sucrose or saccharin.

Oily suspensions may be formulated by suspending the active ingredients in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid and/or copper ascorbate.

Dispersible powders and granules suitable for preparation of an aqueous suspension by the addition of water provide the active ingredient (i.e., copper (I) complex) in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or *arachis* oil, or a mineral oil, for example liquid paraffin or mixtures of these. Suitable emulsifying agents may be naturally occurring gums, for example gum acacia or gum tragacanth; naturally-occurring phosphatide, for example soy bean, lecithin, and esters or partial esters derived from fatty acids and hexitol; anhydrides, for example sorbitan monooleate; and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring or coloring agents. The pharmaceutical compositions may be in the form of a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- and diglycerides. In addition, fatty acids such as oleic acid find use in the preparation of injectables.

Alternatively, the compositions can be administered parenterally in a sterile medium. The copper (I) complexes of the present invention, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition containing copper (I) complexes of the present invention may be added to the animal's feed or drinking water. Optionally, one skilled in the art will recognize that animal feed and drinking products may be formulated such that the animal takes in an effective amount of copper (I) complexes of the present invention via their diet. For example, copper (I) complexes of the present invention may constitute a component of a premix formulated for addition to the feed or drinking water of an animal. Compositions containing copper (I) complexes of the present invention may also be formulated as food or drink supplements for humans.

Preferred embodiments of compositions containing copper (I) complexes of the present invention will have desirable pharmacological properties that include, but are not limited to, oral bioavailability, low toxicity, and desirable in vitro and in vivo half-lives. The half-life of copper (I) complexes of the present invention is inversely proportional to the frequency of dosage of the compounds.

Synthesis of the Copper (I) Complexes

In one embodiment, the present invention provides a method of synthesizing a copper (I) glycinate complex. The method comprises: a) charging a glycinate salt under a stream of inert gas in an alcohol or water; b) heating the glycinate salt in the alcohol or water at between 40° C. to 45° C.; c) adding a copper (I) salt to the alcohol and allowing to reflux for at least 12 hours; and d) evaporating the alcohol or water and washing the copper (I) glycinate complex with alcohol and/or water to remove impurities. In a preferred embodiment, the inert gas is nitrogen. In some implementations, the glycinate salt is charged under a stream of inert gas with an ascorbate salt in an alcohol. In one aspect, the glycinate salt in alcohol is heated for 30 minutes. In a preferred embodiment, the mixture of copper (I) salt and glycinate salt in water is refluxed for between 12 to 16 hours. In some implementations, the mixture of the glycinate salt and copper (I) salt in water is cooled to about 37° C., in a preferred embodiment, the mixture is further cooled by stirring. In a preferred implementation, evaporating the alcohol or water and washing the copper (I) glycinate complex with alcohol and/or water takes place under nitrogen-purge. For example, the water is dried by flushing a pressure filter with nitrogen. Once the collected products on the filter is semi-dry, the drying process continues in a drying plate, under vacuum conditions, at a temperature of 41° C. The isolated crystals of copper (I) glycinate complex prepared in the absence of the ascorbate salt have a lavender purple color, whereas isolated crystals of copper (II) glycinate complex have a blue color.

In an alternate embodiment, the present invention provides a method of synthesizing a copper (I) pyruvate complex. The method comprises: a) charging a pyruvate salt under a stream of inert gas in an alcohol; b) heating the pyruvate salt in the alcohol at about 45° C.; c) adding a copper (I) salt to the alcohol and allowing to reflux for at least 12 hours; and d) evaporating the alcohol and washing the copper (I) pyruvate complex with water to remove impurities. In some implementations, the pyruvate salt is charged under a stream of inert gas with an ascorbate salt in an alcohol. In one aspect, the pyruvate salt in alcohol is heated for 30 minutes. In a preferred embodiment, the mixture of copper (I) salt and pyruvate salt in water is refluxed for between 12 to 16 hours. The isolated crystals of copper (I) pyruvate complex prepared in the absence of the ascorbate salt have an orange-yellow color.

In another embodiment, the present invention provides a method of synthesizing a copper (I) succinate complex. The method comprises: a) charging a succinate salt under a stream of inert gas in an alcohol; b) heating the succinate salt and the ascorbate salt in the alcohol at about 45° C.; c) adding a copper (I) salt to the alcohol and allowing to reflux for at least 12 hours; and d) evaporating the alcohol and washing the copper (I) succinate complex with water to remove impurities. In some implementations, the pyruvate salt is charged under a stream of inert gas with an ascorbate salt in an alcohol. In one aspect, the succinate salt in alcohol is heated for 30 minutes. In a preferred embodiment, the mixture of copper (I) salt and succinate salt in water is refluxed for between 12 to 16 hours. The isolated crystals of copper (I) succinate complex prepared in the absence of the ascorbate salt have a pink color.

In preferred embodiments of the methods of synthesizing a copper (I) glycinate complex, a copper (I) pyruvate complex, or a copper (I) succinate complex, the copper (I) salt is copper (I) chloride. The molar ratios of glycinate salt, pyruvate salt, or succinate salt to the copper (I) salt may be about 3:1, about 3:1.1, about 3:1.2, about 3:1.3, about 3:1.4, about 3:1.5, about 3:1.6, about 3:1.7, or about 3:1.8. The ascorbate salt used may be sodium ascorbate, and the alcohol may be ethanol. The molar ratios of glycinate salt/pyruvate salt/succinate salt to ascorbate salt to copper (I) salt may be about 3:1:1, about 3:1.1:1.1, about 3:1.2:1.2, about 3:1.3:1.3, about 3:1.4:1.4, about 3:1.5:1.5, about 3:1.6:1.6, about 3:1.7:1.7, or about 3:1.8:1.8. In one embodiment, the alcohol is 90% ethanol.

The methods of synthesizing copper (I) complexes may further comprise trituration with organic solvents and/or recrystallization to further purify the copper (I) complexes.

It is to be understood that the foregoing describes preferred embodiments of the present invention and that modifications may be made thereto without departing from the scope or spirit of the present invention as set forth in the claims. Such scope is limited only by the claims below as read in connection with the above specification. Many additional advantages of applicant's invention will be apparent to those skilled in the art from the descriptions, drawings, and the claims set forth herein.

EXAMPLES

Example 1a. Preparation of a Copper (I) Glycinate Complex

Those skilled in the art will recognize various synthetic methodologies that may be employed to prepare non-toxic pharmaceutically acceptable compositions of copper (I) glycinate. One such (representative) example is set forth below.

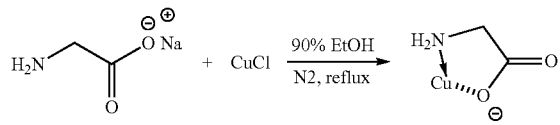

A 100 mL, 3-necked flask was charged with 90% ethanol (EtOH), sodium glycinate and sodium ascorbate under a stream of $N_2$ while charging. The mixture was heated to 45° C. for 30 minutes. Cuprous chloride (aka copper (I) chloride, CuCl or $Cu_2Cl_2$) was then added to the mixture and placed under reflux overnight with $N_2$. The amounts and volumes of each component in the mixture are shown in Table 1. The molar ratio of sodium glycinate:sodium L-ascorbate:cuprous chloride was 3:1:1.

TABLE 1

Reaction mixture for production of copper (I) glycinate

| Compound | Mass (g) | Volume (mL) | Molecular Weight | mmol | Molar Equivalent | Source |
|---|---|---|---|---|---|---|
| Sodium glycinate | 2 | | 97.05 | 20.6079 | 1 | Sigma Aldrich |
| Sodium L-ascorbate | 1.34727 | | 198.11 | 6.80061 | 0.33 | Sigma Aldrich |
| CuCl | 0.67326 | | 99 | 6.80061 | 0.33 | Strem Chemicals |
| 90% EtOH | | 60 | | | | |

A red suspension was filtrated to furnish a small amount of red powder (~100 mg), which was washed with water. The mother liquor was concentrated by evaporation of the ethanol and contained most of the mass as a brown powder.

Proton NMR was performed to identify the copper (I) glycinate product. Proton NMR (dissolved in $D_2O$) of the red powder (~100 mg) indicated no presence of starting material or product.

Proton NMR (dissolved in $D_2O$) of the concentrated mother liquor indicated a single peak at 3.677 ppm and other small peaks between 3.7-4.7 ppm (see FIG. 1). The $D_2O$ solvent peak is at 4.8 ppm.

Figure 2:
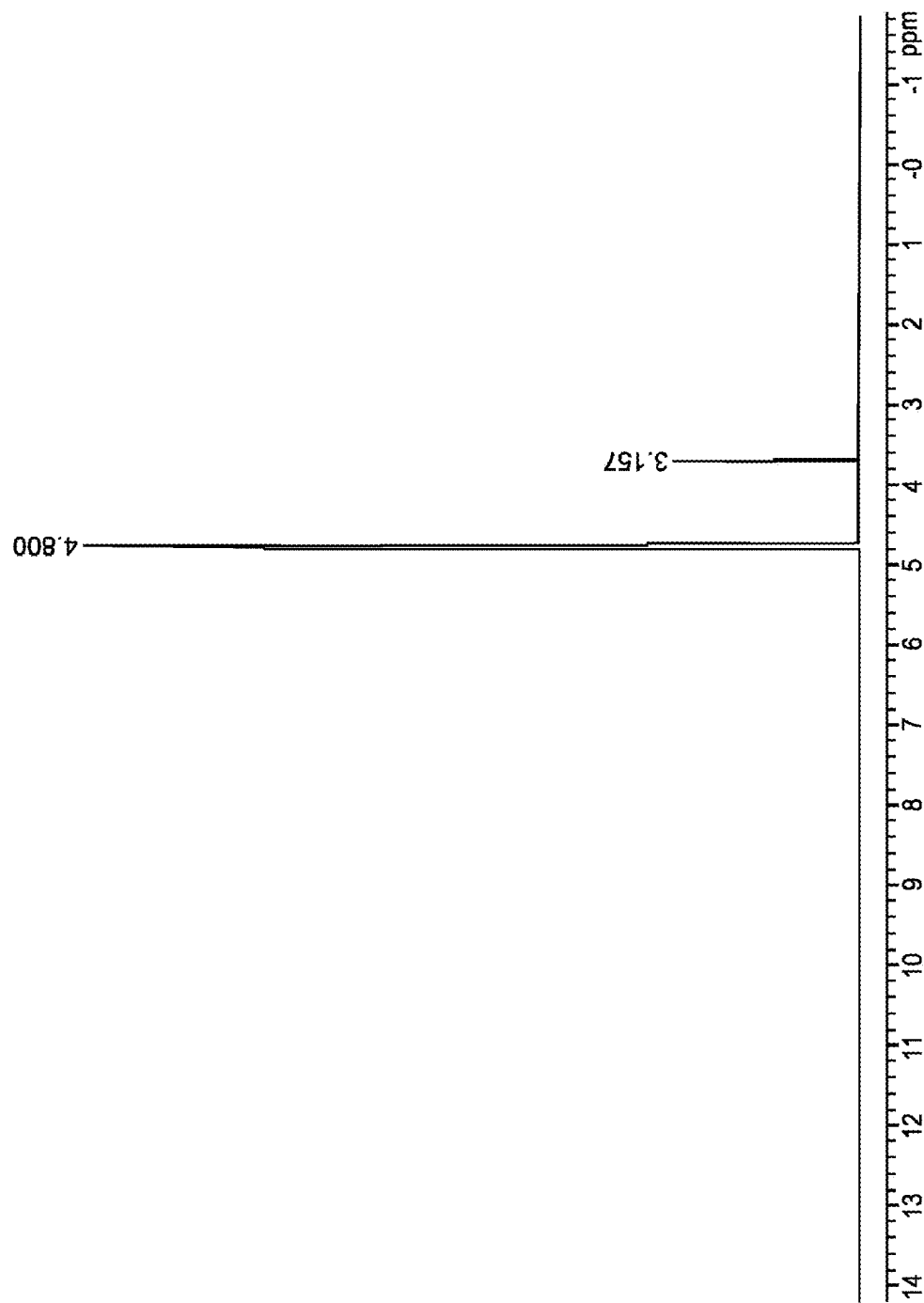
FIG. 2 depicts a proton NMR of sodium glycinate dissolved in $D_2O$.
Figure 3:
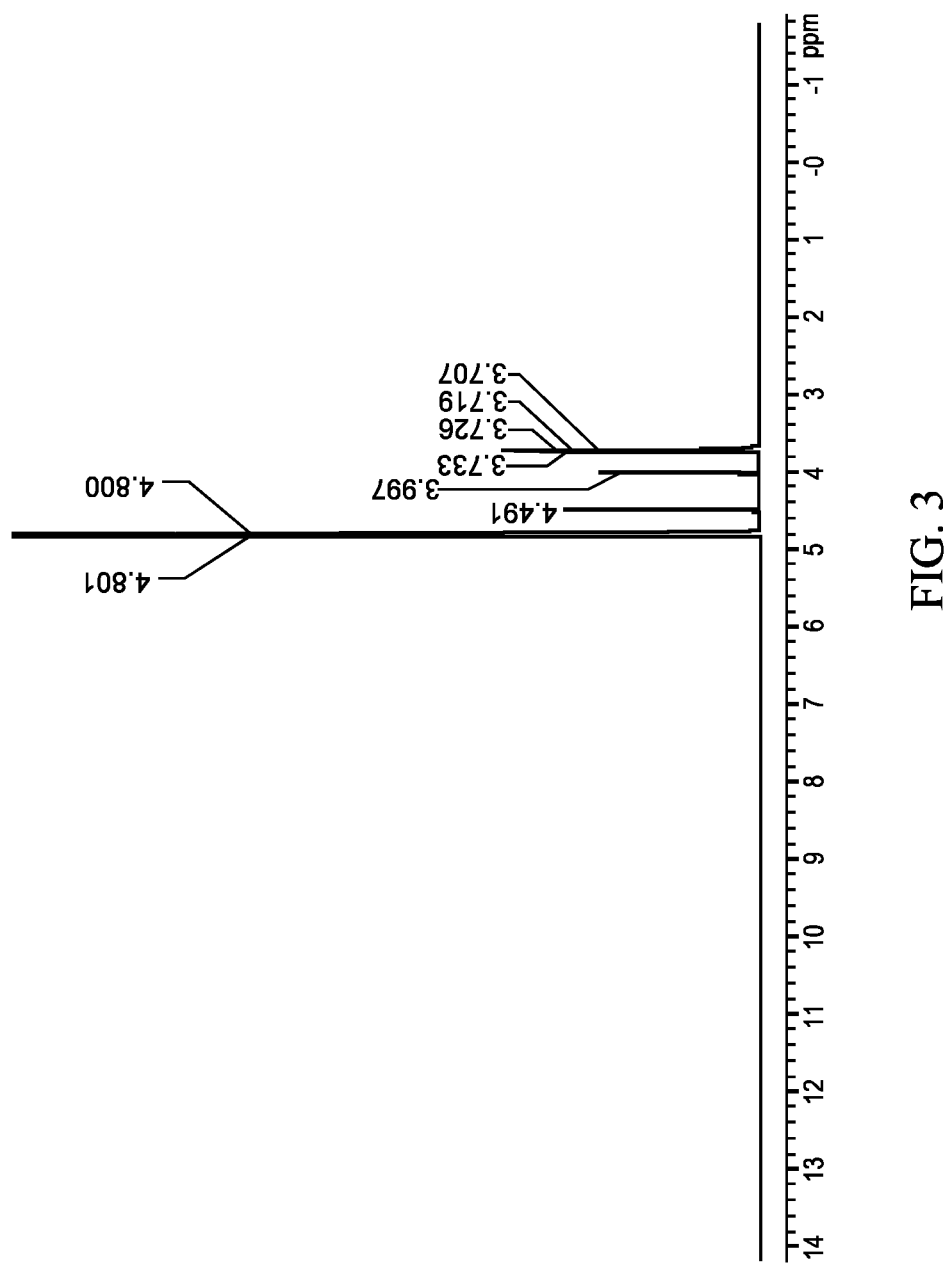
FIG. 3 depicts a proton NMR of sodium ascorbate dissolved in $D_2O$.

Proton NMR (dissolved in $D_2O$) of sodium glycinate indicated a single peak at 3.157 ppm, which corresponds to the methylene ($CH_2$) (see FIG. 2). Proton NMR (dissolved in $D_2O$) of sodium ascorbate indicated the following peaks: 3.70-3.73 ($CH_2$), 3.99 (CHOH), and 4.49 (CH) ppm that correspond to the expected sodium L-ascorbate peaks (see FIG. 3).

In the proton NMR spectrum of the mother liquor there is no presence of sodium glycinate (3.157 ppm) (see FIG. 1). There is a singlet peak at 3.67 ppm believed to correspond to the desired Cu (I) chelated methylene ($CH_2$) product, copper (I) glycinate.

Example 1b. Preparation of a Copper (I) Glycinate Complex

| Component | Qty | F.W. | Moles | Equiv. |
|---|---|---|---|---|
| 1) Glycine | 6.7 g | 75.07 | 0.0893 | 3 |
| 2) Water | 70 ml | — | — | 1 |
| 3) Ethanol | 350 ml | — | — | 5 |
| 4) Cu(I)Cl | 2.95 g | 99 | 0.0298 | 1 |

The preparation process requires assembly of a nitrogen-purged 500 ml reaction flask equipped with a mechanical stirrer, temperature probe/controller, reflux condenser, solid addition funnel and heating mantle and nitrogen purge. Under nitrogen purge, the reaction flask is charged with glycine (6.7 g or 0.0893 mol) and deionized water (70 ml).

The resulting mixture is stirred to complete dissolution. The dissolved mixture is heated to 40-45° C. while remaining under nitrogen. The reaction flask is then charge with ethanol (350 ml) under nitrogen and then heated back to 40-45° C. Via solid addition funnel, charge the cuprous chloride slowly while maintaining a temperature of 40-5° C. during the addition. Turn off the heat and allow the mixture to exothermal (about 5-10° C. exothermal is typical). The mixture is cooled to about 37° C. and stirred for approximately one hour. Afterwards, the reaction is removed from heat and sparged with nitrogen for approximately one hour. The final product is filtered using a pressure filter under nitrogen purge. The collected product was rinsed with ethanol (200 ml) two times with 15 minutes between each rinse. The collected product on the filter is then flushed with nitrogen for at least 45 minutes until semi-dry. The collected product on the filter is transferred to a drying dish and dried under vacuum at 41° C. The drying dish is placed at an angle of 30° to 45° to facilitate drying and formation of clean crystals. Yield: ~95% of copper (I) glycinate, a lavender purple microcrystalline solid.

Example 2. SEM Analysis of Copper (I) Glycinate Complex

Figure 4:
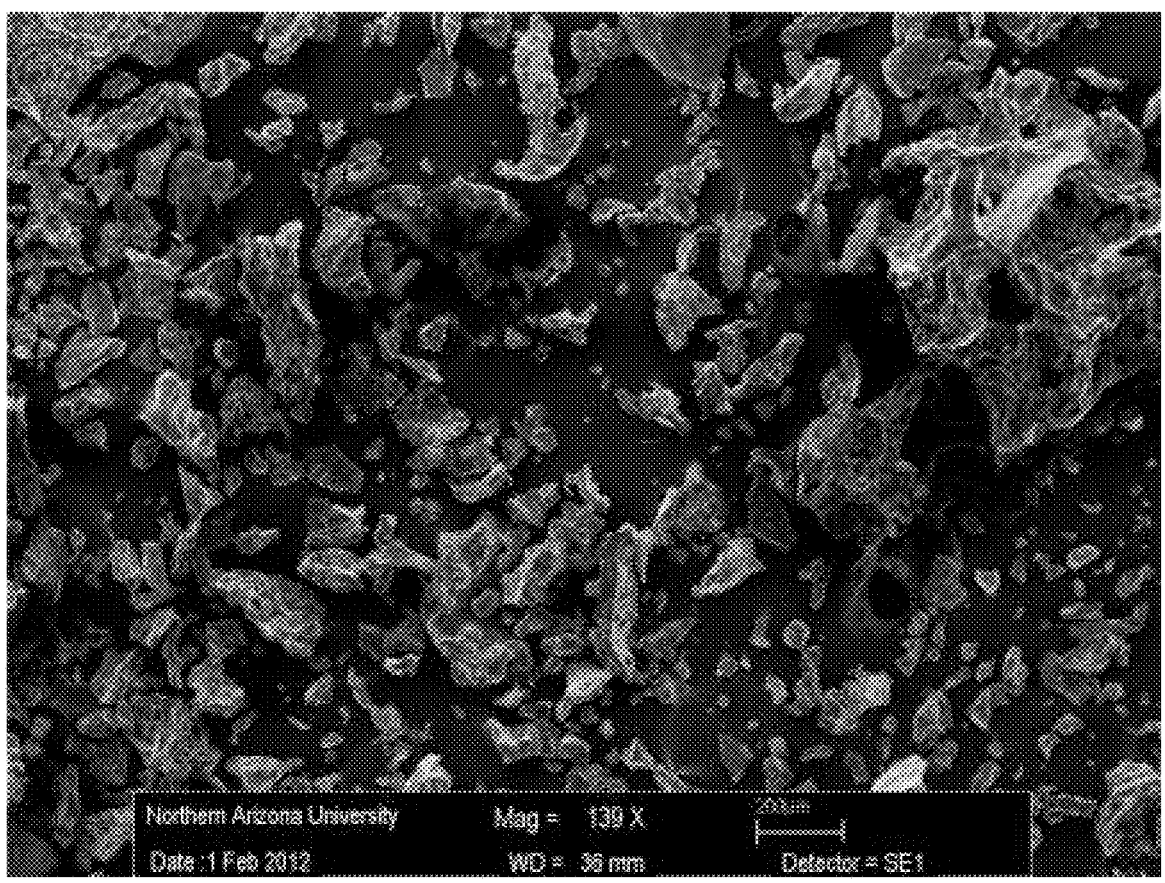
FIG. 4 depicts an image of a copper (I) glycinate complex captured with a scanning electron microscope (SEM). The scale bar represents 200 µm.
Figure 5:
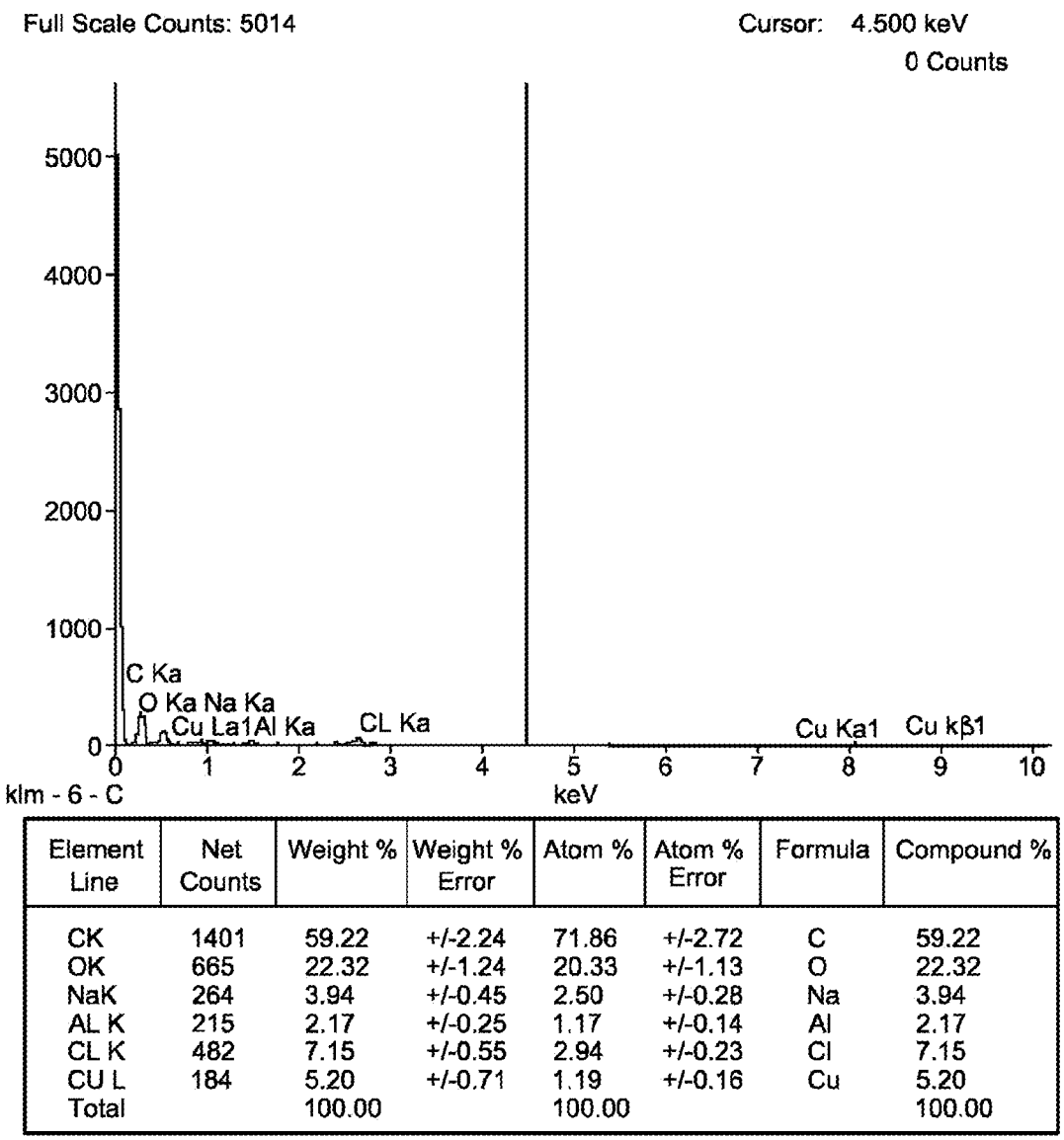
FIG. 5 depicts the results of an Energy Dispersive Spectroscopy analysis on an SEM (EDS-SEM) with a copper (I) glycinate complex. The elements identified in the analysis are carbon (C), oxygen (O), sodium (Na), aluminum (Al), chlorine (CO, and copper (Cu).
Figure 6A:
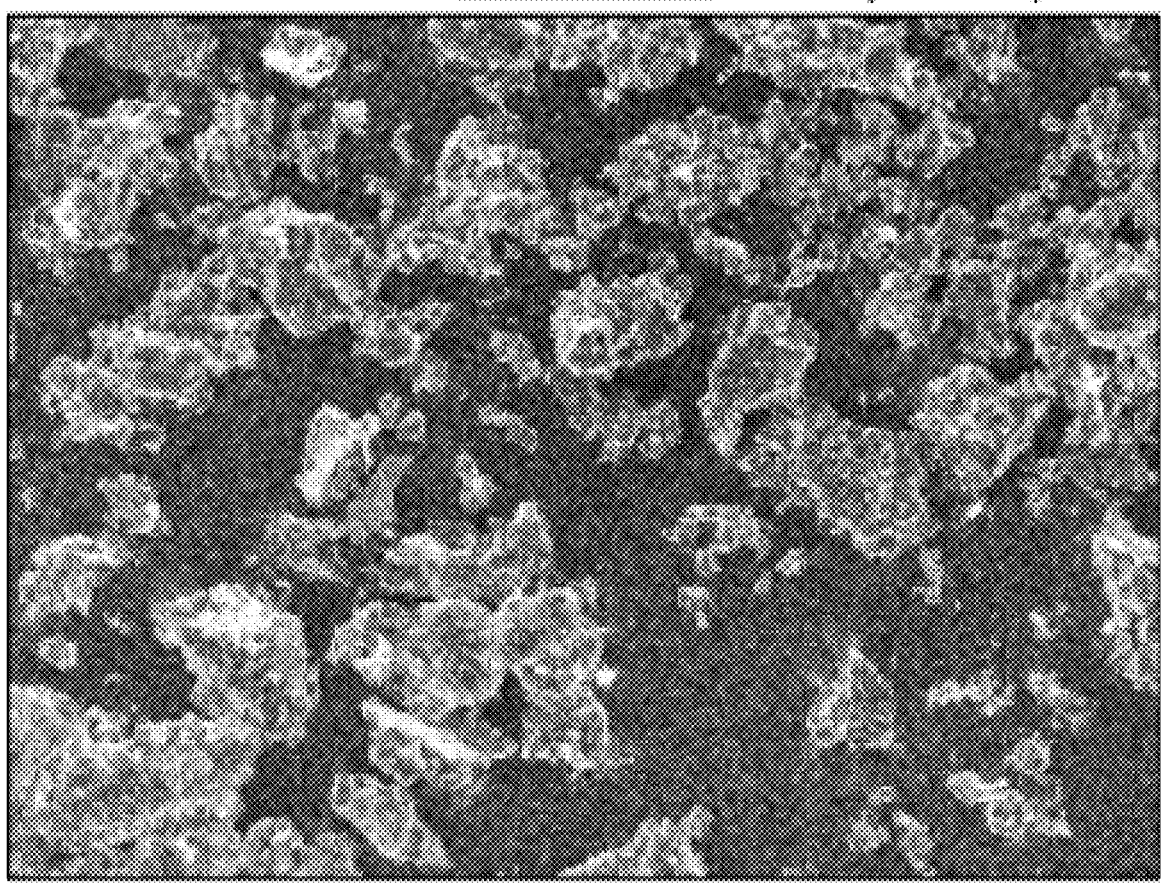
FIGS. 6A and 6B depict two versions of the SEM image of a copper (I) glycinate complex that was analyzed by EDS-SEM. The scale bar represents 50 µm.
Figure 6B:
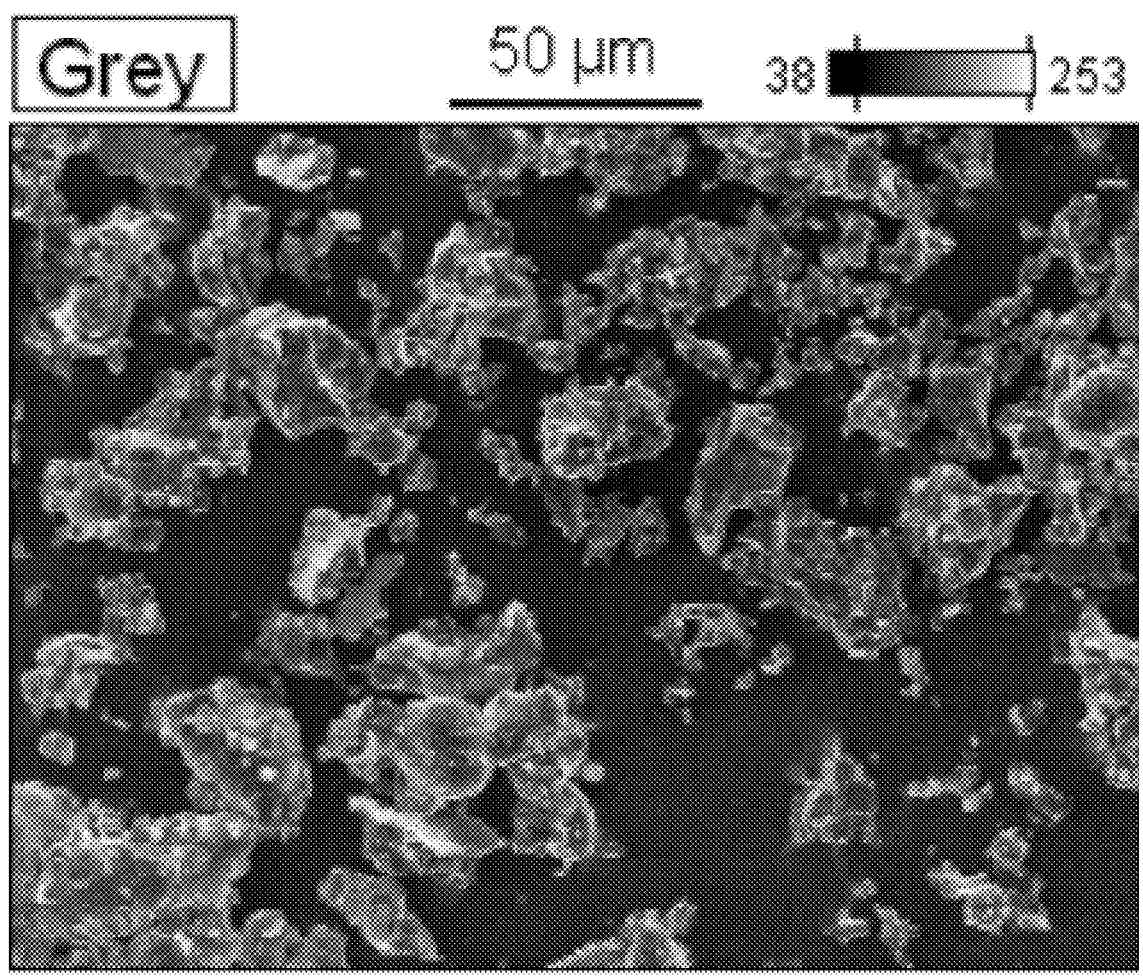
Figure 7:
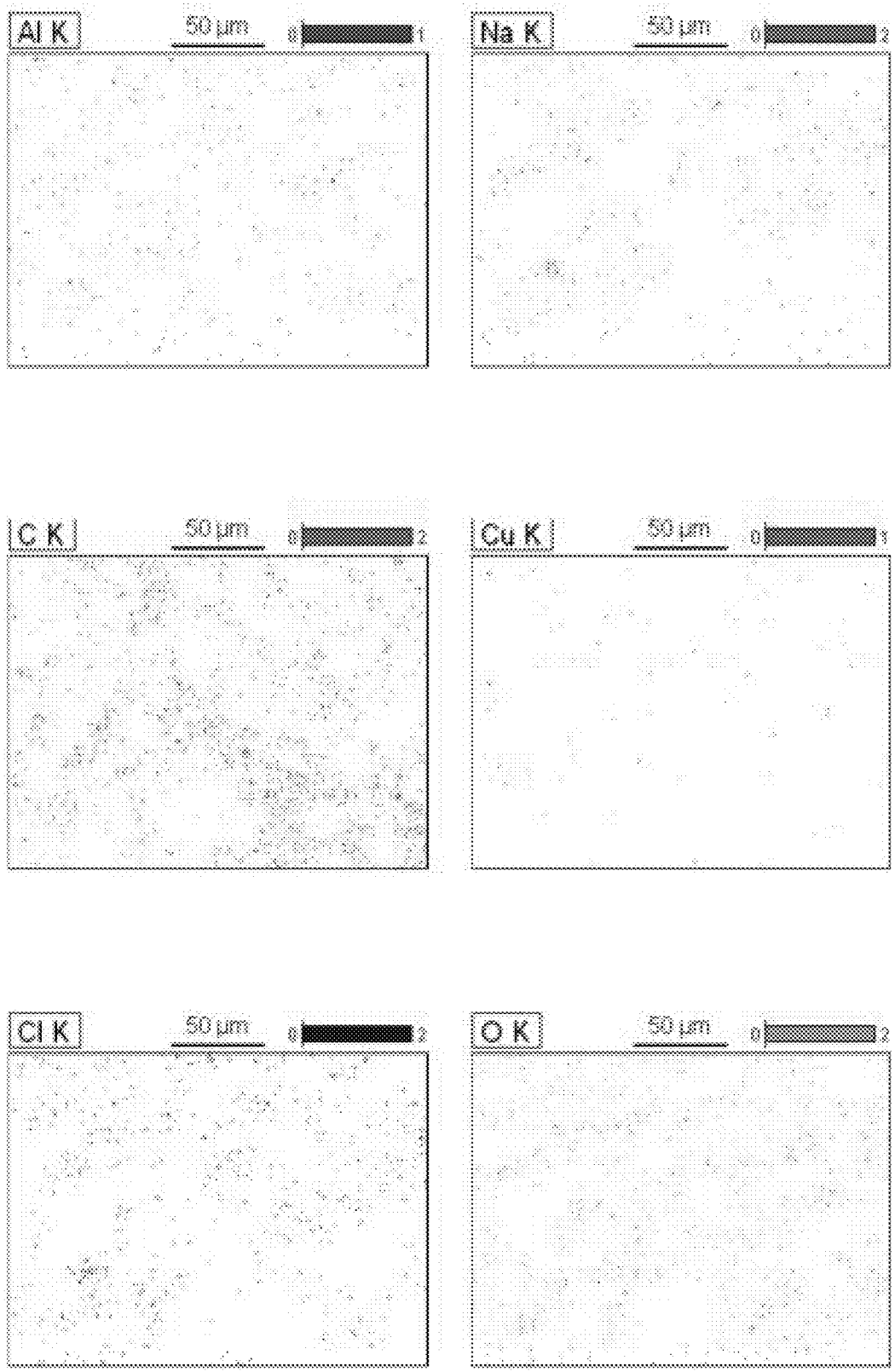
FIG. 7 depicts the distribution and relative proportion (intensity) of the specified elements over the area scanned by the EDS-SEM of a copper (I) glycinate complex.

The copper (I) glycinate complex synthesized in Example 1 was analyzed with an SEM, and various images of the copper (I) glycinate complex were captured (see FIG. 4 for a representative image). An Energy Dispersive Spectroscopy analysis on the SEM (EDS-SEM) was run with the energy-dispersive spectrometer set at an acceleration voltage of 15.0 kV. The EDS-SEM analysis revealed the presence of carbon I, oxygen (O), and copper (Cu) in the copper (I) glycinate complex. Sodium (Na), aluminum (Al), and chlorine (Cl) were also identified as impurities present in the copper (I) glycinate complex. See FIGS. 5-7.

Example 3. Preparation of a Copper (I) Pyruvate Complex

Those skilled in the art will recognize various synthetic methodologies that may be employed to prepare non-toxic pharmaceutically acceptable compositions of copper (I) pyruvate. One such (representative) example is set forth below.

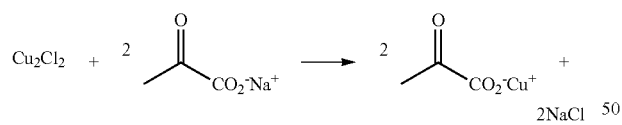

A 100 mL, 3-necked flask was charged with 90% ethanol (EtOH), sodium pyruvate and sodium ascorbate under a stream of $N_2$ while charging. The mixture was heated to 45° C. for 30 minutes. Cuprous chloride was then added to the mixture and placed under reflux overnight with $N_2$. The molar ratio of sodium pyruvate:sodium L-ascorbate:cuprous chloride was 3:1:1. The resulting product was concentrated by evaporation of the ethanol and washed with water to remove residual sodium chloride.

Example 4. SEM Analysis of Copper (I) Pyruvate Complex

Figure 8:
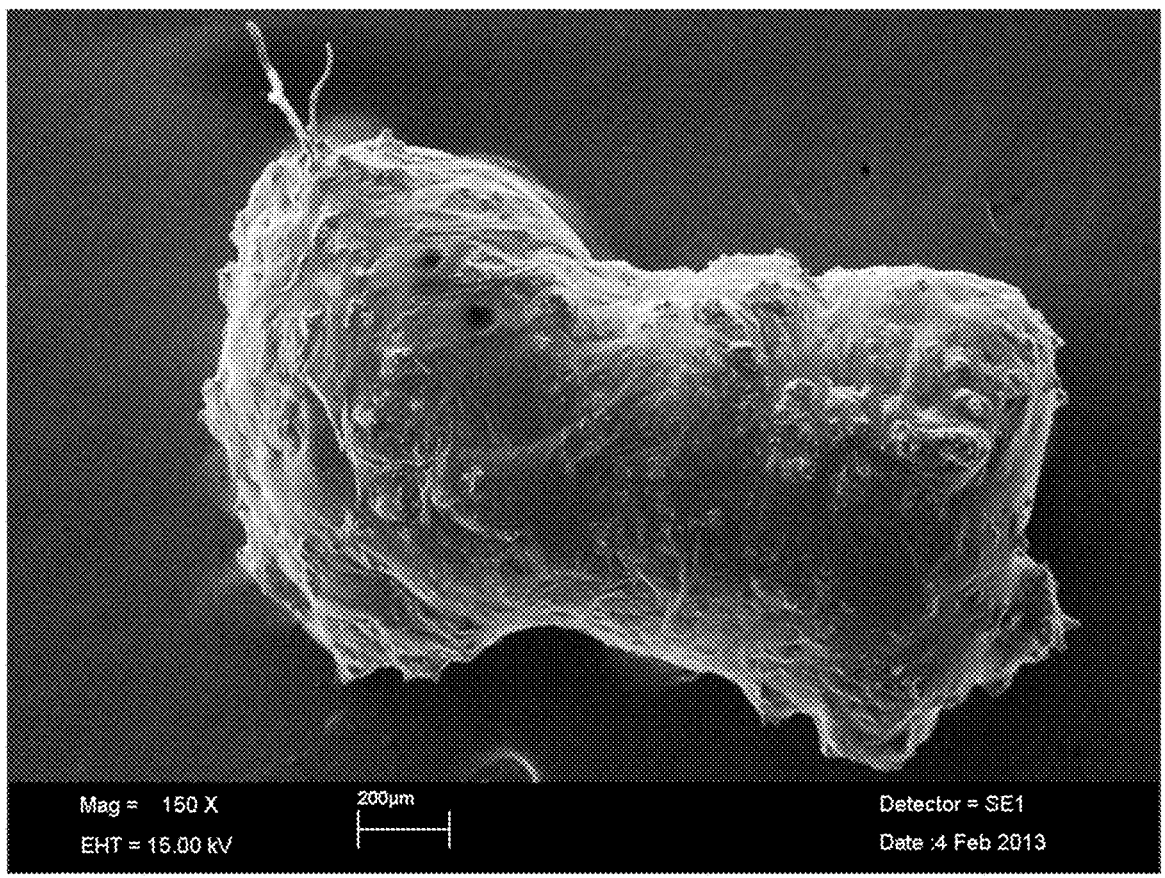
FIG. 8 depicts an image of a copper (I) pyruvate complex captured with an SEM. The scale bar represents 200 µm.
Figure 9:
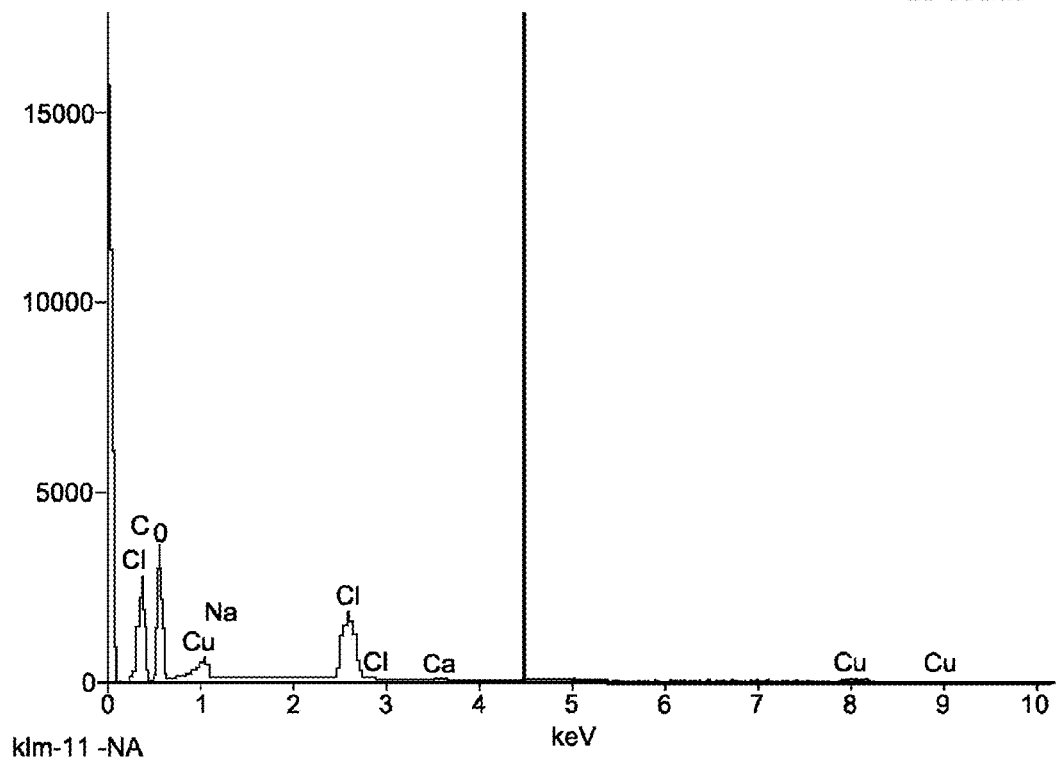
FIG. 9 depicts the results of an EDS-SEM analysis with a copper (I) pyruvate complex. The elements identified in the analysis are carbon (C), oxygen (O), sodium (Na), chlorine (Cl), calcium (Ca), and copper (Cu).
Figure 10A:
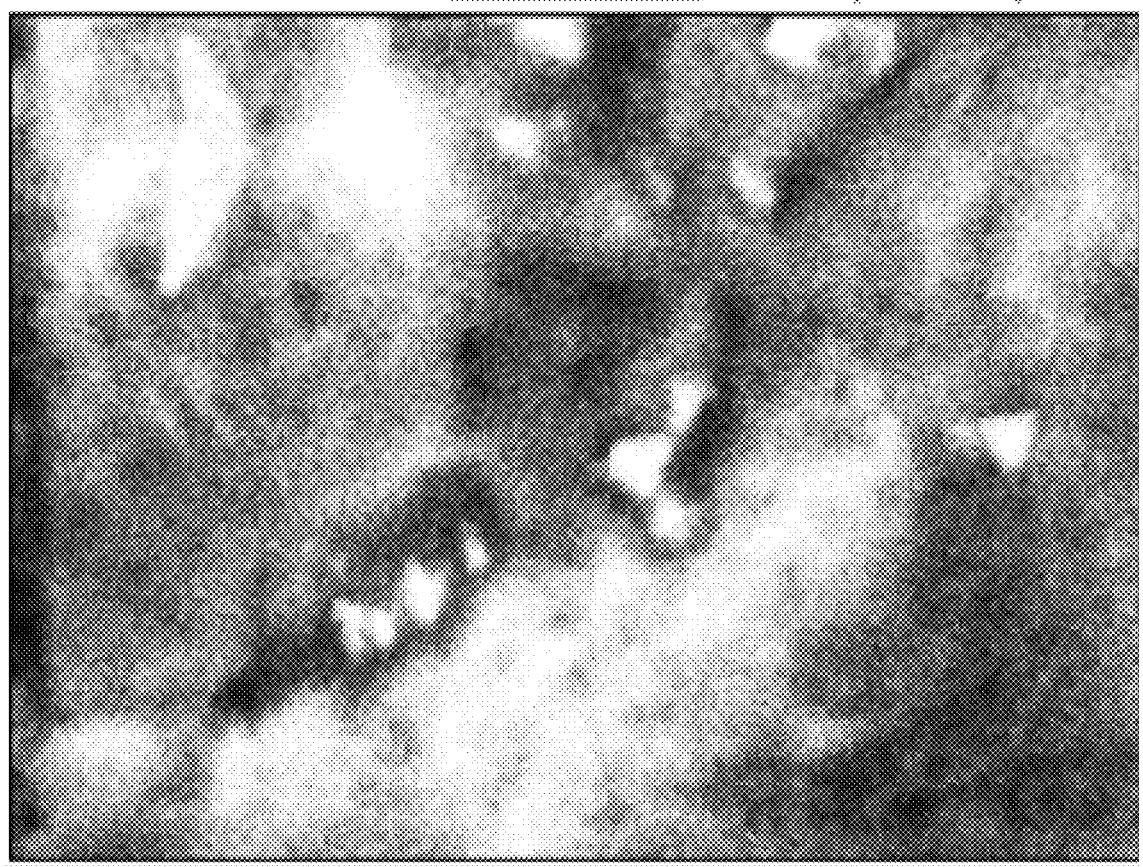
FIGS. 10A and 10B depict two versions of an SEM image of a copper (I) pyruvate complex that was analyzed by EDS-SEM. The scale bar represents 500 µm.
Figure 10B:
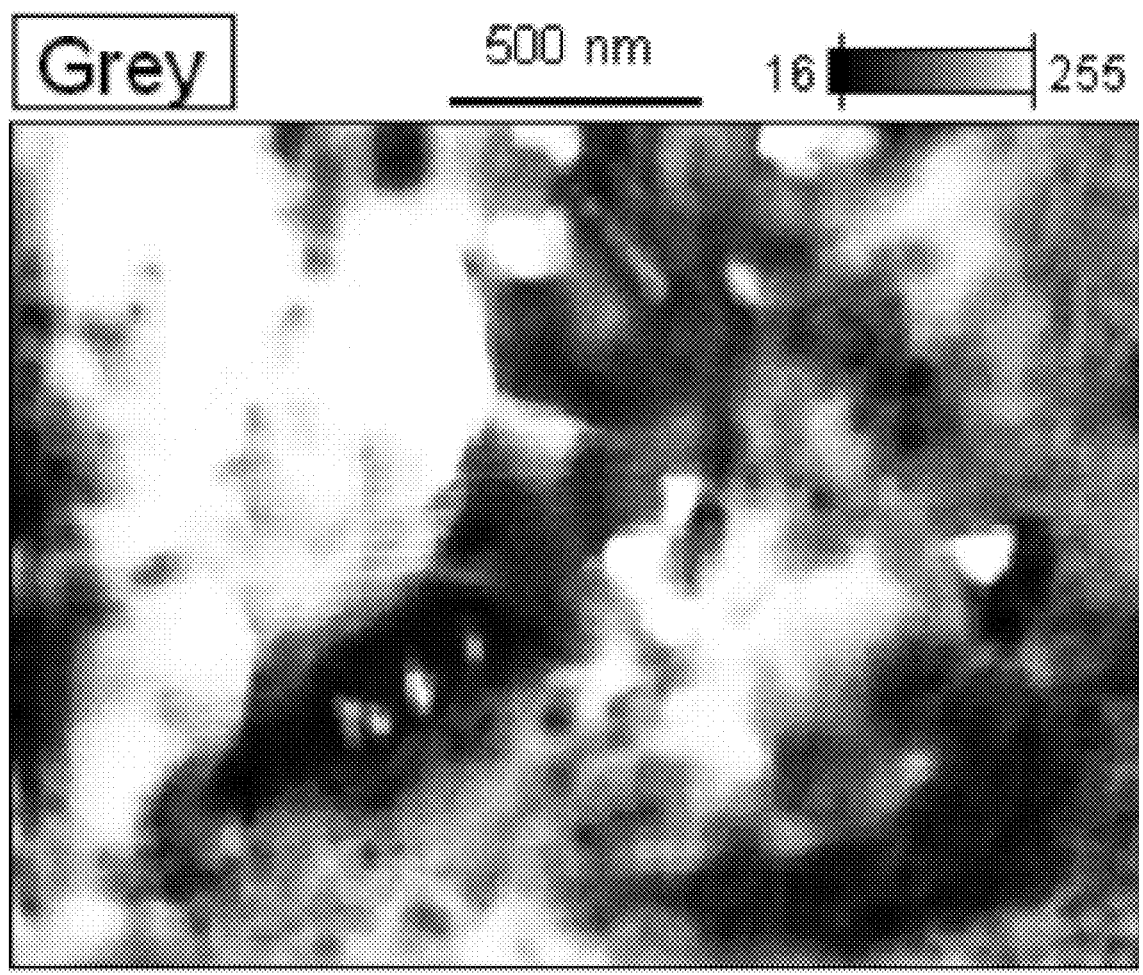
Figure 11:
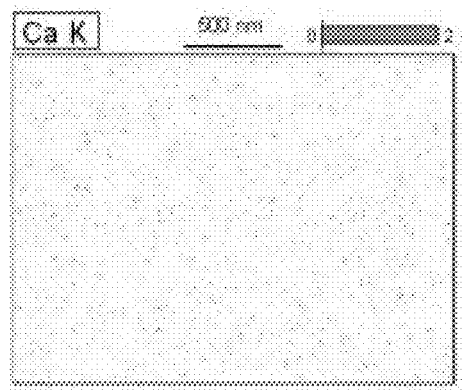
FIG. 11 depicts the distribution and relative proportion (intensity) of the specified elements over the area scanned by the EDS-SEM of a copper (I) pyruvate complex.
Figure 11:
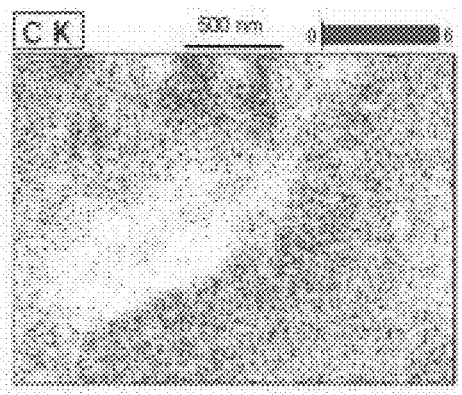
Figure 11:
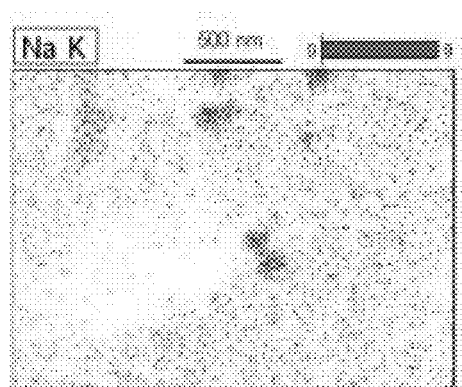
Figure 11:
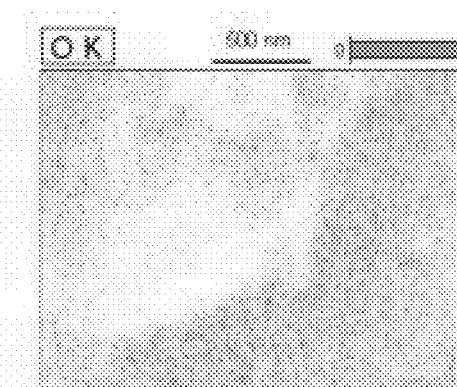
Figure 11:
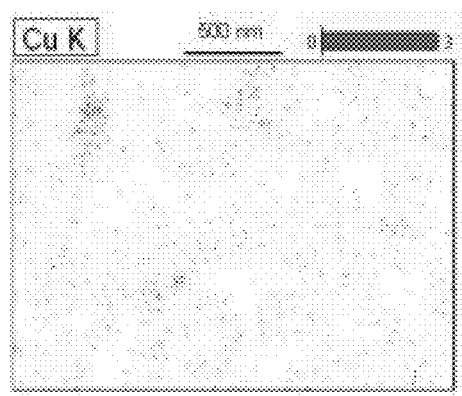
Figure 11:
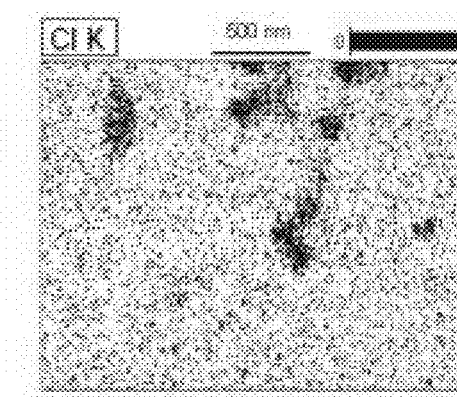

The copper (I) pyruvate complex synthesized in Example 3 was analyzed with an SEM, and various images of the copper (I) pyruvate complex were captured (see FIG. 8 for a representative image). An EDS-SEM analysis was run with the energy-dispersive spectrometer set at an acceleration voltage of 20.0 kV. The EDS-SEM analysis revealed the presence of carbon (C), oxygen (O), and copper (Cu) in the copper (I) pyruvate complex. Sodium (Na), chlorine (CO, and calcium (Ca) were also identified as impurities present in the copper (I) pyruvate complex. See FIGS. 9-11.

Example 5. Preparation of a Copper (I) Succinate Complex

Those skilled in the art will recognize various synthetic methodologies that may be employed to prepare non-toxic pharmaceutically acceptable compositions of copper (I) succinate. One such (representative) example is set forth below.

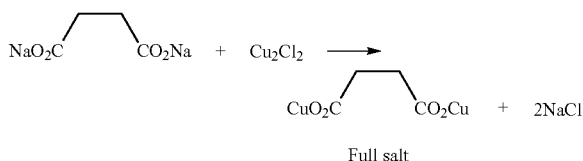

Full salt

A 100 mL, 3-necked flask was charged with 90% ethanol (EtOH), sodium succinate and sodium ascorbate under a stream of $N_2$ while charging. The mixture was heated to 45° C. for 30 minutes. Cuprous chloride was then added and the mixture placed under reflux overnight with $N_2$. The molar ratio of sodium succinate:sodium L-ascorbate:cuprous chloride was 3:1:1. The resulting product was concentrated by evaporation of the ethanol and washed with water to remove residual sodium chloride.

Because succinic acid possesses two acidic groups, there are at least two different species of salt possible. The first is the hemi form, in which only one of the carboxylic acids is in the copper salt form, while the other is the full salt form in which there are two coppers to one succinate, one at each carboxylate. Therefore, the product of this synthesis reaction may contain a mixture of the hemi salt and the full salt as shown below.

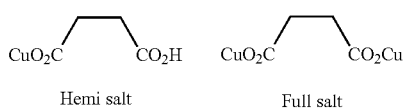

Hemi salt          Full salt

Example 6. SEM Analysis of Copper (I) Succinate Complex

Figure 12:
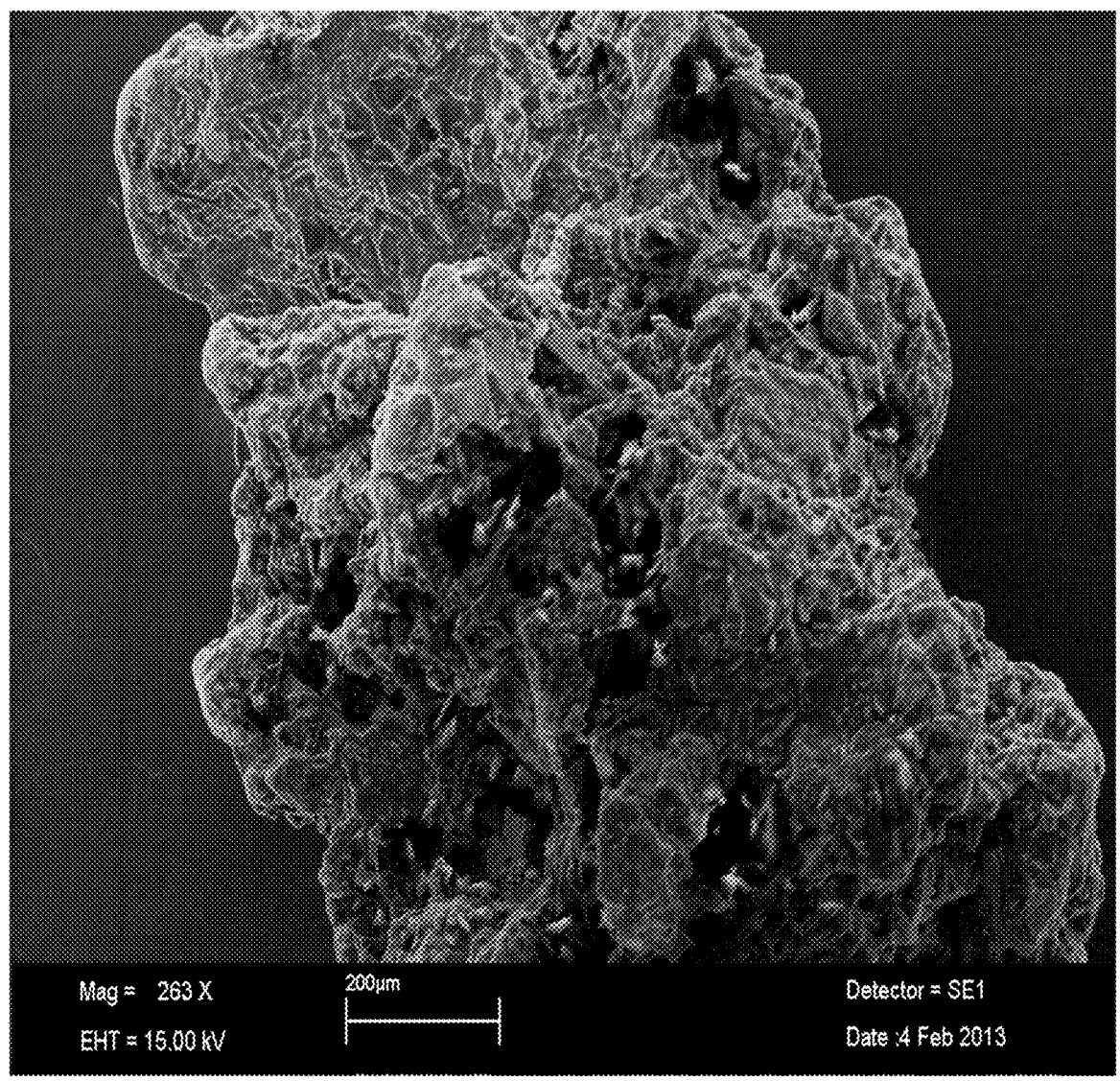
FIG. 12 depicts an image of a copper (I) succinate complex captured with an SEM. The scale bar represents 200 µm.
Figure 13:
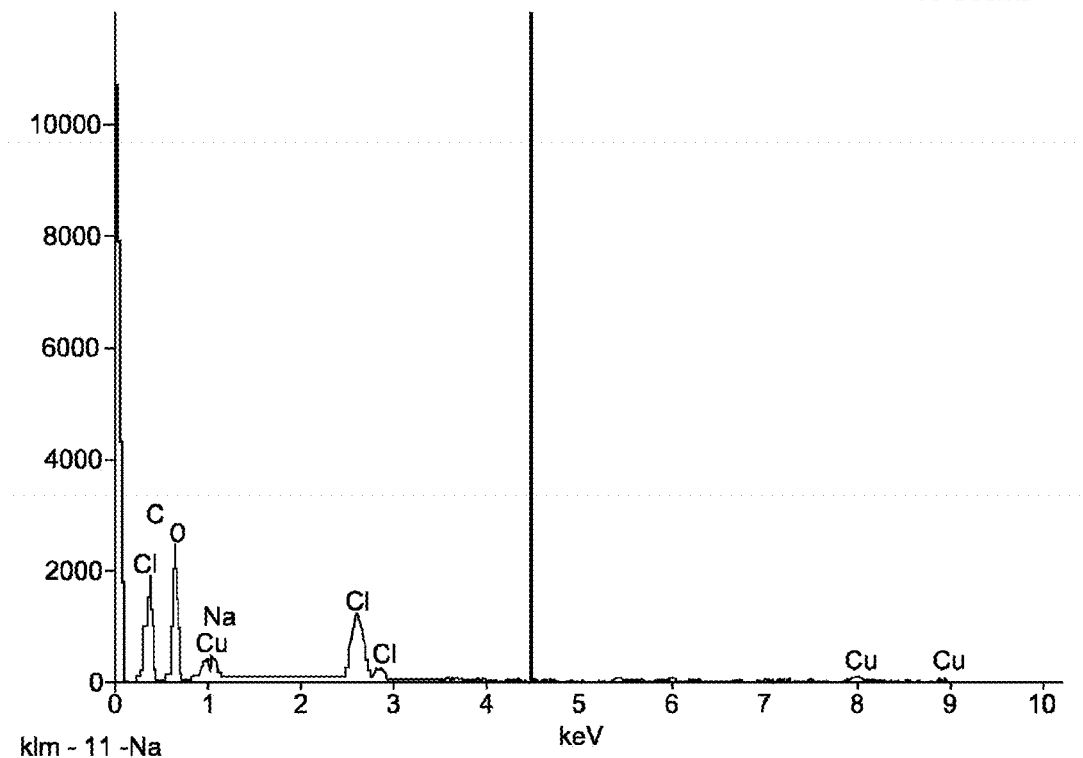
FIG. 13 depicts the results of an EDS-SEM analysis with a copper (I) succinate complex. The elements identified in the analysis are carbon (C), oxygen (O), sodium (Na), chlorine (Cl), and copper (Cu).
Figure 14A:
FIGS. 14A and 14B depict two versions of an SEM image of a copper (I) succinate complex that was analyzed by EDS-SEM. The scale bar represents 500 µm.
Figure 14B:
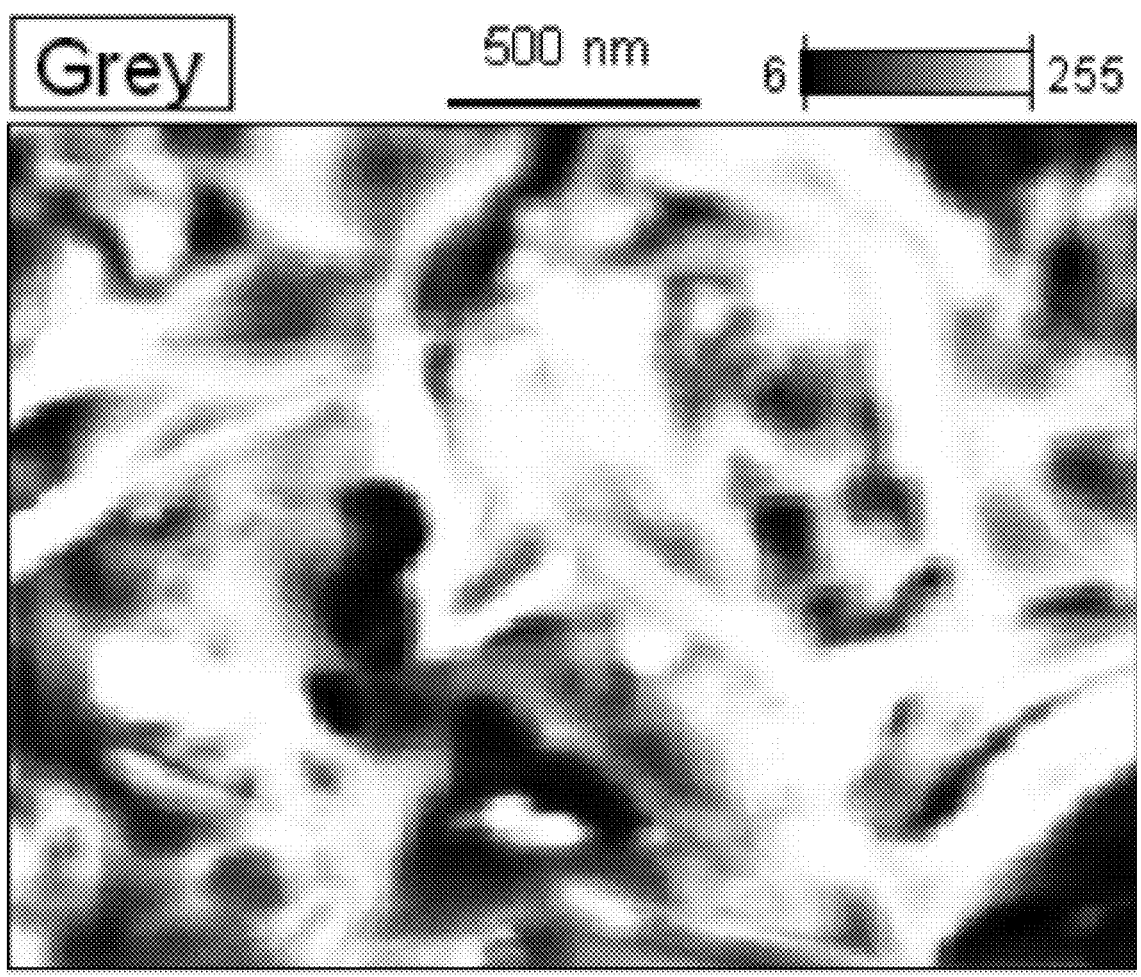
Figure 15:
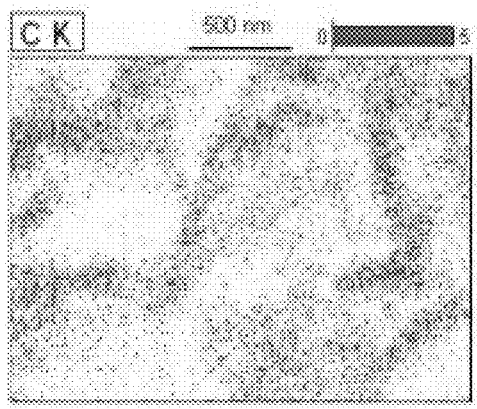
FIG. 15 depicts the distribution and relative proportion (intensity) of the specified elements over the area scanned by the EDS-SEM of a copper (I) succinate complex.
Figure 15:
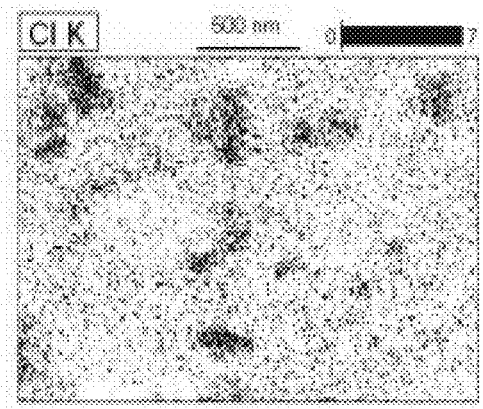
Figure 15:
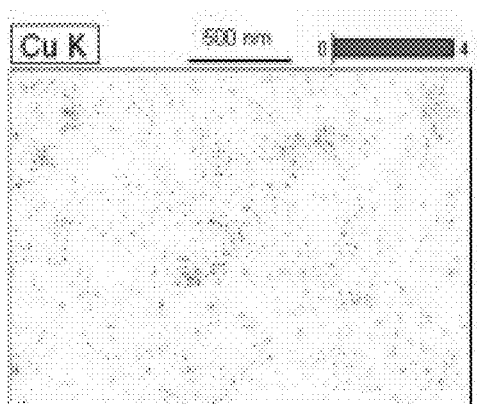
Figure 15:
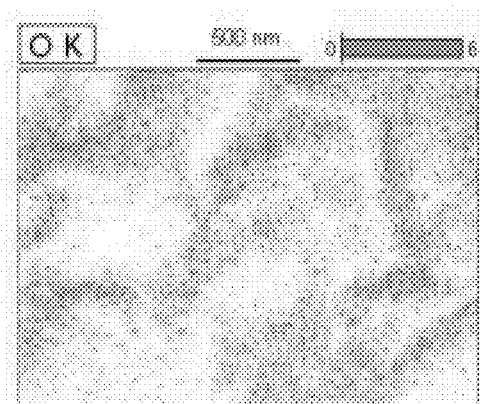
Figure 15:
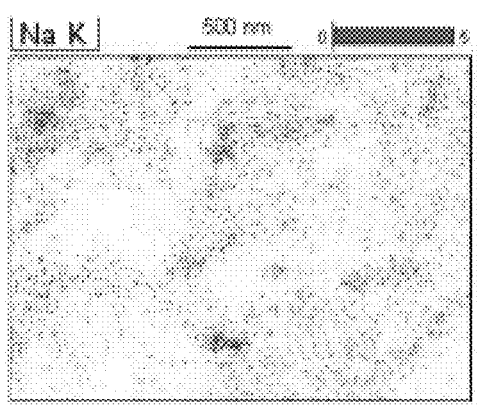

The copper (I) succinate complex synthesized in Example 5 was analyzed with an SEM, and various images of the copper (I) pyruvate complex were captured (see FIG. 12 for a representative image). An EDS-SEM analysis was run with the energy-dispersive spectrometer set at an acceleration voltage of 20.0 kV. The EDS-SEM analysis revealed the presence of carbon (C), oxygen (O), and copper (Cu) in the copper (I) succinate complex. Sodium (Na) and chlorine (Cl) were also identified as impurities present in the copper (I) pyruvate complex. See FIGS. 13-15.

Example 7. In Vitro Effects of Copper (I) Glycinate Complex

Figure 16:
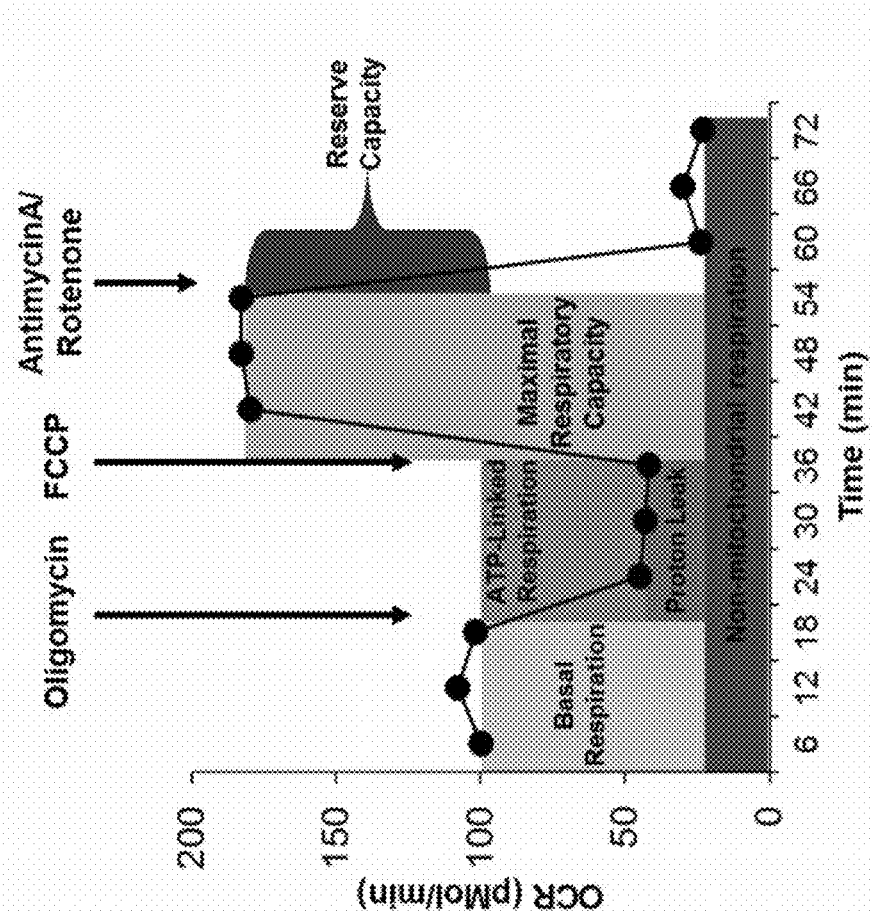
FIG. 16 depicts the time course of the XF Cell Mito Stress Test.
Figure 17:
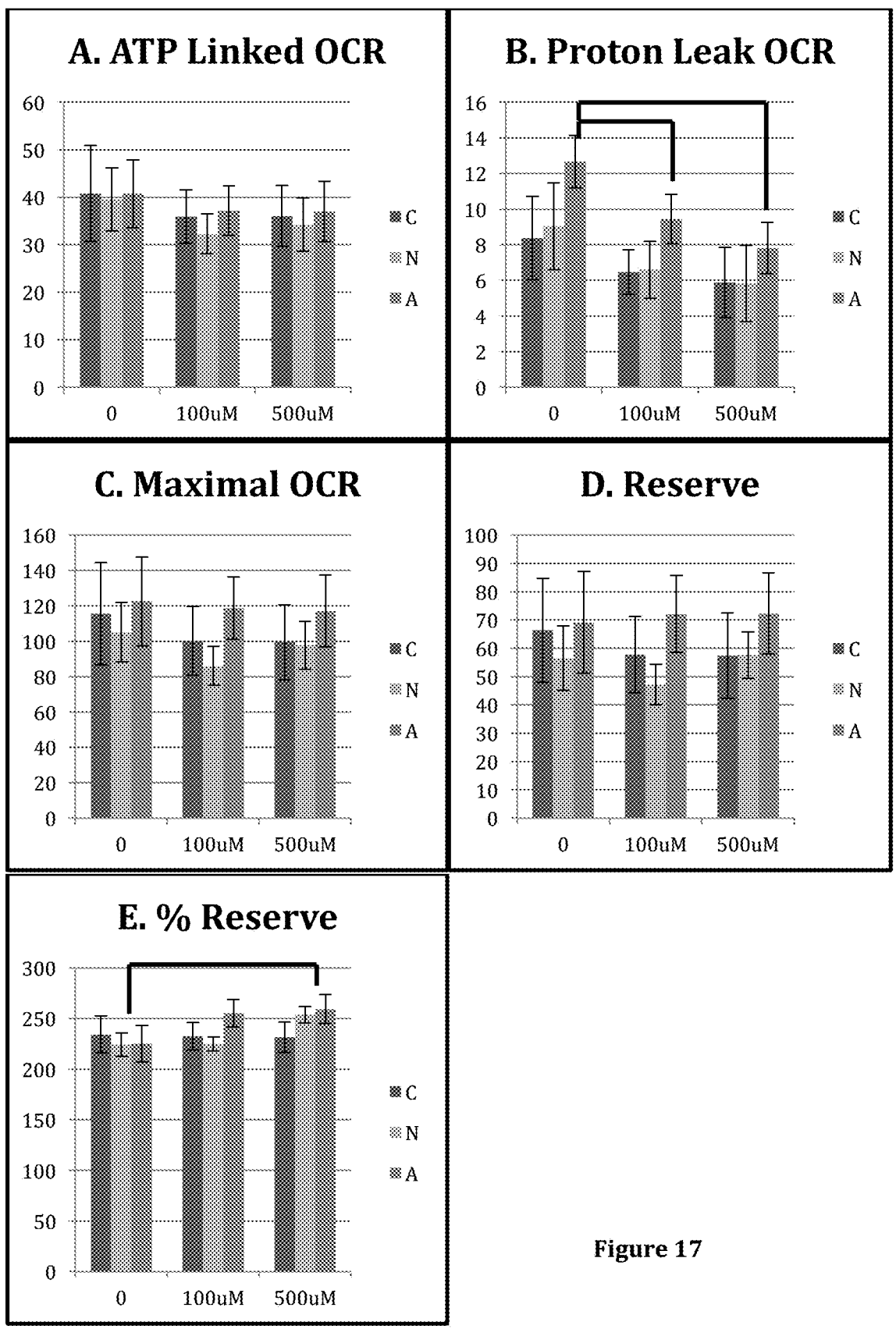
FIG. 17 depicts the compares results of the XF cell Mito Stress Test in lymphoblasts from control individuals (C) and autistic subjects with (A) or without mitochondrial dysfunction (N). The figure also compares the effect of administering 100 µM or 500 µM copper (I) glycinate complex on the oxygen consumption rate of these cells.

The copper (I) glycinate complex synthesized in Example 1b was used in a mitochondrial stress test using the XF Cell Mito Stress Test kit (Agilent, Wilmington, Del.). The cells studies were lymphoblasts from normal subjects (C), lymphoblasts from autistic donors without mitochondrial dysfunction (N), and lymphoblasts from autistic donors with mitochondrial dysfunction (A). ATP-linked respiration, proton leak, maximal respiratory capacity, and reserve capacity were determined as measured by the cells' oxygen consumption rate. FIG. 16 depicts the time points during the course of mitochondrial stress tests that are relevant for determining ATP-linked respiration, proton leak, maximal respiratory capacity, and reserve capacity. FIG. 17 depicts the results of the stress test with that compares the administration of 100 µM or 500 µM of the copper (I) glycinate to the respiration of these cells without administration of the copper (I) complex. Panel B of FIG. 17 shows that 500 µM of the copper (I) glycinate significantly reduced proton leak lymphoblasts with mitochondrial dysfunction. Mitochondrial dynfunction in cells was determined using the methods of the Frye lab, which was described in Rose et al., "Oxidative stress induces mitochondrial dysfunction in a subset of autistic lymphoblastoid cell lines," *Transl Psychiatry,* 2014 4:e377.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

It is to be understood that the methods set forth hereinabove describe preferred synthetic methodologies and that modifications thereto may be made without departing from the scope or spirit of the invention. Such scope is limited only by the claims below as read in connection with the above specification. Many additional synthetic methodologies and additional advantages of applicant's invention will be apparent to those skilled in the art from the above descriptions and the claims below.

We claim:

1. A method of synthesizing a copper (I) complex comprising:
    a) charging a salt selected from the group consisting of: a glycinate salt, a pyruvate salt, and a succinate salt, under a stream of inert gas in an alcohol or water;
    b) heating the salt in the alcohol or water at about 40-45° C.;
    c) adding a copper (I) salt to the alcohol or water and allowing to reflux for at least 12 hours to produce a copper (I) complex;
    d) evaporating the alcohol or water from the copper (I) complex.

2. The method of claim 1, further comprising trituration with organic solvents and/or recrystallization to further purify the copper (I) complex.

3. The method of claim 1, wherein the salt is heated at about 45° C. for 30 minutes.

4. The method of claim 1, wherein a molar ratio of the salt to the copper (I) salt is about 3:1.5.

5. The method of claim 1, wherein the mixture of the salt and the copper (I) salt in alcohol is refluxed for between 12 to 16 hours.

6. The method of claim 1, wherein evaporating the alcohol or water from the copper (I) complex comprises using a pressure filter under nitrogen purge to collect the copper (I) complex and flushing the filter with nitrogen for at least 45 minutes.

7. The method of claim 6, wherein collected copper (I) complex is washed with ethanol using the pressure filter under nitrogen purge.

8. The method of claim 6, further comprising drying the collected copper (I) complex under vacuum at about 41° C.

9. The method of claim 8, wherein drying collected copper (I) complex comprises drying the copper (I) complex in a dry plate positioned at an angle of 30° to 45°.

* * * * *